US012735726B2

(12) United States Patent
Mouradian et al.

(10) Patent No.: US 12,735,726 B2
(45) Date of Patent: Sep. 15, 2026

(54) TARGETING DELTAFosB FOR TREATMENT OF DYSKINESIA

(71) Applicants: Rutgers, The State University of New Jersey, New Brunswick, NJ (US); Emory University, Atlanta, GA (US)

(72) Inventors: Mary M. Mouradian, Princeton, NJ (US); Stella Papa, Atlanta, GA (US); Jie Zhang, East Brunswick, NJ (US); Goichi Beck, Osaka (JP)

(73) Assignees: RUTGERS, THE STATE UNIVERSITY OF NEW JERSEY, New Brunswick, NJ (US); EMORY UNIVERSITY, Atlanta, GA (US)

( * ) Notice: Subject to any disclaimer, the term of this patent is extended or adjusted under 35 U.S.C. 154(b) by 1141 days.

(21) Appl. No.: 17/755,504

(22) PCT Filed: Nov. 2, 2020

(86) PCT No.: PCT/US2020/058515

§ 371 (c)(1),
(2) Date: Apr. 29, 2022

(87) PCT Pub. No.: WO2021/087445

PCT Pub. Date: May 6, 2021

(65) Prior Publication Data

US 2022/0364118 A1 Nov. 17, 2022

Related U.S. Application Data

(60) Provisional application No. 62/929,176, filed on Nov. 1, 2019.

(51) Int. Cl.

| | |
|---|---|
| ***C12N 15/861*** | (2006.01) |
| ***A61P 25/14*** | (2006.01) |
| ***C12N 15/113*** | (2010.01) |

(52) U.S. Cl.

CPC ............ *C12N 15/861* (2013.01); *A61P 25/14* (2018.01); *C12N 15/113* (2013.01); *C12N 2750/14122* (2013.01)

(58) Field of Classification Search

None

See application file for complete search history.

(56) References Cited

U.S. PATENT DOCUMENTS

| | | | | |
|---|---|---|---|---|
| 2005/0079610 A1* | 4/2005 | Polisky | .......... | C12Y 104/03003 435/375 |
| 2010/0310473 A1 | 12/2010 | Liu et al. | | |
| 2018/0298380 A1 | 10/2018 | Gao et al. | | |
| 2019/0282639 A1* | 9/2019 | Lahusen | ............. | C12N 9/1077 |

OTHER PUBLICATIONS

NCBI Reference Sequence: NM_001347586.1 (1996) (Year: 1996).*
Al-Rubeai M and Merten OW. Viral Vectors for Gene Therapy. Methods in Molecular Biology. (Year: 2011).*
Engeln, et al. Selective inactivation of striatal FosB/DeltaFosB-expressing neurons alleviates L-DOPA-induced dyskinesia. Biological Psychiatry. 79:354-61. (Year: 2016).*
Nakabeppu, et al. NCBI Reference Sequence. (Year: 1991).*
Bastide, et al. Immediate-early gene expression in structures outside the basal ganglia is associated to L-DOPA-induced dyskinesia. Neurobiology of Disease. 2014; 62:172-192. (Year: 2014).*
Yen, et al. An alternative spliced form of FosB is a negative regulator of transcriptional activation and transformation by Fos proteins. Proceedings of the National Academy of Sciences USA. 1991; 88:5077-5081. (Year: 1991).*
Moore, et al. Short Hairpin RNA (shRNA): Design, Delivery, and Assessment of Gene Knockdown. Methods in Molecular Biology. 2010; 629:141-158. (Year: 2010).*

* cited by examiner

*Primary Examiner* — Allison M Fox
*Assistant Examiner* — Gina Pronzati
(74) *Attorney, Agent, or Firm* — FOX ROTHSCHILD LLP

(57) ABSTRACT

Compositions, non-viral vectors, recombinant viruses, and recombinant viral vectors for inhibiting ΔFosB expression or activity in a cell and for treating dyskinesia in a subject (e.g., a human patient having Parkinson's disease and Levodopa-induced dyskinesia) include a nucleic acid sequence encoding a shRNA specific for ΔFosB. Methods of using these compositions, non-viral vectors, recombinant viruses, and recombinant viral vectors are also described herein. These compositions, non-viral vectors, recombinant viruses, and recombinant viral vectors and methods of use provide novel therapies for dyskinesia based on the reduction of ΔFosB expression and/or activity.

14 Claims, 19 Drawing Sheets

Specification includes a Sequence Listing.

SEQUENCE LISTING

```
<160> NUMBER OF SEQ ID NOS: 23

<210> SEQ ID NO 1
<211> LENGTH: 19
<212> TYPE: RNA
<213> ORGANISM: Artificial Sequence
<220> FEATURE:
<223> OTHER INFORMATION: SYNTHETIC CONSTRUCT

<400> SEQUENCE: 1

cuggccgagu gaaguucaa                                                   19


<210> SEQ ID NO 2
<211> LENGTH: 19
<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 2

uugaacuuca cucggccag                                                   19
```

-continued

<210> SEQ ID NO 3
<211> LENGTH: 877
<212> TYPE: DNA
<213> ORGANISM: Homo sapiens

<400> SEQUENCE: 3
atgtttcagg ctttccccgg agactacgac tccggctccc ggtgcagctc ctcaccctct 60
gccgagtctc aatatctgtc ttcggtggac tccttcggca gtccacccac cgccgccgcc 120
tcccaggagt gcgccggtct cggggaaatg cccggttcct tcgtgcccac ggtcaccgcg 180
atcacaacca gccaggacct ccagtggctt gtgcaaccca ccctcatctc ttccatggcc 240
cagtcccagg ggcagccact ggcctcccag cccccggtcg tcgaccccta cgacatgccg 300
ggaaccagct actccacacc aggcatgagt ggctacagca gtggcggagc gagtggcagt 360
ggtgggcctt ccaccagcgg aactaccagt gggcctgggc ctgcccgccc agcccgagcc 420
cggcctagga gaccccgaga ggagacgctc accccagagg aagaggagaa gcgaagggtg 480
cgccgggaac gaaataaact agcagcagct aaatgcagga accggcggag ggagctgacc 540
gaccgactcc aggcggagac agatcagttg gaggaagaaa aagcagagct ggagtcggag 600
atcgccgagc tccaaaagga gaaggaacgt ctggagtttg tgctggtggc ccacaaaccg 660
ggctgcaaga tcccctacga agaggggccc gggccgggcc cgctggcgga gtgaagttca 720
agtcctcggc gacccccttcc ccgttgttaa cccttcgtac acttcttcgt ttgtcctcac 780
ctgcccggag gtctccgcgt tcgccggcgc ccaacgcacc agcggcagtg accagccttc 840
cgatcccctg aactcgccct ccctcctcgc tctgtga 877

<210> SEQ ID NO 4
<211> LENGTH: 19
<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 4
cuggcggagu gaaguucaa 19

<210> SEQ ID NO 5
<211> LENGTH: 65
<212> TYPE: RNA
<213> ORGANISM: Rattus norvegicus
<220> FEATURE:
<221> NAME/KEY: misc_feature
<222> LOCATION: (35)..(35)
<223> OTHER INFORMATION: N is nucleotides deleted due to alternative
      splicing.

<400> SEQUENCE: 5
ggggccaggc ccgcuggccg aggugagaga uuugnacaca cagugaaguu caaguccucg 60
gcgac 65

<210> SEQ ID NO 6
<211> LENGTH: 44
<212> TYPE: RNA
<213> ORGANISM: Rattus norvegicus

<400> SEQUENCE: 6
ggggccaggc ccgcuggccg agugaaguuc aaguccucgg cgac 44

<210> SEQ ID NO 7
<211> LENGTH: 19

<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 7
cgcuggccga gugaaguuc 19

<210> SEQ ID NO 8
<211> LENGTH: 19
<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 8
ccgcuggccg agugaaguu 19

<210> SEQ ID NO 9
<211> LENGTH: 21
<212> TYPE: RNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (20)..(21)
<223> OTHER INFORMATION: N is dT

<400> SEQUENCE: 9
cuggccgagu gaaguucaan n 21

<210> SEQ ID NO 10
<211> LENGTH: 21
<212> TYPE: RNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (20)..(21)
<223> OTHER INFORMATION: N is dT

<400> SEQUENCE: 10
uugaacuuca cucggccagn n 21

<210> SEQ ID NO 11
<211> LENGTH: 21
<212> TYPE: RNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (20)..(21)
<223> OTHER INFORMATION: N is dT

<400> SEQUENCE: 11
cgcuggccga gugaaguucn n 21

<210> SEQ ID NO 12
<211> LENGTH: 21
<212> TYPE: RNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (20)..(21)

<223> OTHER INFORMATION: N is dT

<400> SEQUENCE: 12
gaacuucacu cggccagcgn n 21

<210> SEQ ID NO 13
<211> LENGTH: 21
<212> TYPE: RNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (20)..(21)
<223> OTHER INFORMATION: N is dT

<400> SEQUENCE: 13
ccgcuggccg agugaaguun n 21

<210> SEQ ID NO 14
<211> LENGTH: 21
<212> TYPE: RNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (20)..(21)
<223> OTHER INFORMATION: N is dT

<400> SEQUENCE: 14
aacuucacuc ggccagcggn n 21

<210> SEQ ID NO 15
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 15
ctggccgagt gaagttcaa 19

<210> SEQ ID NO 16
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 16
ttgaacttca ctcggccag 19

<210> SEQ ID NO 17
<211> LENGTH: 19
<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 17
gaacuucacu cggccagcg 19

<210> SEQ ID NO 18
<211> LENGTH: 19
<212> TYPE: RNA
<213> ORGANISM: ARTIFICIAL SEQUENCE

-continued

```
<220> FEATURE:
<223> OTHER INFORMATION: SYNTHETIC CONSTRUCT

<400> SEQUENCE: 18

aacuucacuc ggccagcgg                                                19


<210> SEQ ID NO 19
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 19

gacgtcaata atgacgtatg                                               20


<210> SEQ ID NO 20
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 20

ggtaatagcg atgactaata cg                                            22


<210> SEQ ID NO 21
<211> LENGTH: 19
<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 21

aguacugcuu acgauacgg                                                19


<210> SEQ ID NO 22
<211> LENGTH: 20
<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 22

ccguaucgua agcaguacuu                                               20


<210> SEQ ID NO 23
<211> LENGTH: 19
<212> TYPE: RNA
<213> ORGANISM: ARTIFICIAL SEQUENCE
<220> FEATURE:
<223> OTHER INFORMATION: SYNTHETIC CONSTRUCT

<400> SEQUENCE: 23

uugaacuuca cuccgccag                                                19
```

TARGETING DELTAFosB FOR TREATMENT OF DYSKINESIA

CROSS-REFERENCE TO RELATED APPLICATION

This application claims priority to U.S. Provisional Patent Application No. 62/929,176 filed Nov. 1, 2019, which is incorporated herein by reference in its entirety.

FEDERALLY SPONSORED RESEARCH

This invention was made with government support under grant no. R01NS073994 awarded by the National Institutes of Health. The government has certain rights in the invention.

FIELD OF THE INVENTION

The invention relates generally to the fields of medicine, neurology, neuroscience, molecular biology, and virology. In particular, the invention relates to compositions, vectors, viruses, kits and methods for treating Levodopa-induced dyskinesia (LID) in a subject.

BACKGROUND

Long-term dopamine replacement therapy in Parkinson's disease (PD) leads to the development of motor complications such as abnormal involuntary movements (AIMs) known as Levodopa-induced dyskinesia (also known as L-Dopa-induced dyskinesia) (LID) (Calabresi et al. 2010 The Lancet. Neurology 9(11):1106-1117). Motor symptoms of PD are caused by loss of dopaminergic innervation in the striatum. Although L-Dopa, the dopamine (DA) precursor molecule, is the most effective drug for PD, long-term use of L-Dopa is associated with serious side effects such as LID. To date, the treatment of LID is limited to a nonselective and weak Nmethyl-D-aspartate (NMDA) receptor antagonist, amantadine (Verhagen et al., 1998 Neurology 50(5):1323-1326), or the invasive alternative of surgery for DBS (Herzog et al., 2007 Movement disorders 22(5):679-684). Improved therapies for LID are greatly needed.

SUMMARY

The effect of gene therapy using a recombinant Adeno-Associated Virus (rAAV) vector including a nucleic acid encoding shRNA specific for ΔFosB (rAAV-shRNA ΔFosB) to suppress the development of LID in the model of PD has been shown. Lowering striatal ΔFosB by gene silencing is an effective and feasible therapeutic approach to improve LID in chronic PD patients with dyskinesia. Described herein are compositions, vectors, viruses, kits and methods for decreasing ΔFosB expression or activity in a subject (e.g., a subject with PD and LID) and ameliorating, or treating LID in a subject. The compositions, vectors, viruses, kits and methods all include a nucleic acid encoding shRNA specific for ΔFosB for inhibiting ΔFosB expression or activity. Several studies have shown that the transcription factor ΔFosB, a truncated form of FosB, plays an important role in the development of dyskinesias. Specifically, the experiments described below in Example 2 that were conducted in a rodent model of PD demonstrated that the transgenic ΔFosB overexpression in the striatum induces rapid development of AIMs in the absence of the typically required repeated L-DOPA treatment. To confirm the key role of this transcription factor, whether inhibiting ΔFosB expression reduces and/or delays AIMs development was investigated. As described in Example 2 below, it was discovered that AIMs scores were significantly reduced in the rats injected with rAAV-ΔFosB shRNA compared to animals injected with the control vector over the course of chronic L-dopa treatment. The experimental results described herein demonstrate that ΔFosB gene silencing using the vectors (viral vectors, non-viral vectors), compositions and methods described herein is a useful therapeutic approach for LID.

Accordingly, described herein is a recombinant viral vector including (a) a heterologous polynucleotide sequence including a nucleic acid sequence encoding at least one shRNA specific for ΔFosB, wherein the at least one shRNA has at least 90% or more sequence identity with the sequence of SEQ ID NO: 1 (CUGGCCGAGUGAAGUUCAA) and/or at least 90% or more sequence identity with the sequence of SEQ ID NO: 2 (UUGAACUUCACUCGGCCAG), and (b) inverted terminal repeat (ITR) sequences flanking the heterologous polynucleotide sequence. The sequence of SEQ ID NO: 2 is the antisense strand of the sequence of SEQ ID NO: 1. In some embodiments, the at least one shRNA includes the sequence of SEQ ID NO: 4. The antisense strand of the sequence of SEQ ID NO: 4 is UUGAACUU-CACUCCGCCAG (SEQ ID NO: 23). The recombinant viral vector can be, as examples, a rAAV vector or a recombinant lentiviral vector. In some embodiments, the at least one shRNA includes an shRNA having at least 90% or more sequence identity with the sequence of SEQ ID NO: 1 (e.g., an shRNA including the sequence of SEQ ID NO: 4) and an shRNA having at least 90% or more sequence identity with the sequence of SEQ ID NO: 2 (e.g., an antisense strand of SEQ ID NO: 4). In such embodiments, the heterologous polynucleotide sequence can further include a loop sequence. A recombinant lentivirus including the recombinant viral vector is described herein. A rAAV including the recombinant viral vector (rAAV vector) is also described herein. The rAAV can include capsid proteins from one or more of the serotypes: AAV1, AAV2, AAV2/1, AAV4, AAV5, AAV8, AAV9, AAV10, AAV11, AAV12, and AAV13. Compositions including any of the recombinant viral vectors (e.g., rAAV vector, recombinant lentivirus vector) or any of the recombinant viruses (e.g., rAAV, recombinant lentivirus) are described herein. Compositions can also include a pharmaceutically acceptable carrier.

Also described herein is a method of reducing ΔFosB expression in a cell (e.g., human cells). The method includes contacting (e.g., transfecting, transducing, infecting) the cell(s) with any of the recombinant viral vectors (e.g., rAAV vectors, recombinant lentivirus vectors) any of the recombinant viruses (e.g., rAAV, recombinant lentivirus) and any of the compositions described herein. A method of treating dyskinesia in a subject (e.g., human having PD and dyskinesia) includes administering to the subject any of the recombinant viral vectors, any of the recombinant viruses, and any of the compositions described herein. In an embodiment of the method, the dyskinesia is LID. Typically, in the method, the subject is a mammal (e.g., human) having PD. In the method, administration of a recombinant viral vector (e.g., rAAV vector), a recombinant virus (e.g., rAAV), or composition as described herein decreases or eliminates abnormal involuntary movements in the subject. In some embodiments of the method, the mammal is administered the recombinant viral vector (e.g., rAAV vector, recombinant lentivirus vector) the recombinant virus (e.g., rAAV, recombinant lentivirus) or the composition via injection or infusion.

Further described herein is a kit for reducing ΔFosB expression in a cell or treating dyskinesia in a subject. The kit includes: a recombinant viral vector (e.g., rAAV vector, recombinant lentivirus vector), recombinant virus (e.g., rAAV, recombinant lentivirus), or composition as described herein; instructions for use; and packaging. In a typical embodiment, the kit is used for treating LID in a human subject suffering from LID and PD.

Also described herein is a non-viral vector including a heterologous polynucleotide sequence including an siRNA nucleic acid specific for ΔFosB. In the non-viral vector, the siRNA has at least 90% or more sequence identity with the sequence of SEQ ID NO: 9 and at least 90% or more sequence identity with the sequence of SEQ ID NO: 10. In some embodiments, the heterologous polynucleotide sequence further includes a loop sequence. The non-viral vector can be, for example, a cationic lipid, a cationic polymer, or an inorganic nanoparticle. Compositions including the non-viral vector are described herein. A kit for reducing ΔFosB expression in a cell or treating dyskinesia in a subject includes a non-viral vector as described herein, instructions for use, and packaging.

Yet further described herein is a method of reducing ΔFosB expression in a cell that includes contacting the cell with a composition including a non-viral vector as described herein. A method of treating dyskinesia in a subject includes administering to the subject a composition including a non-viral vector as described herein.

As used herein, "protein" and "polypeptide" are used synonymously to mean any peptide-linked chain of amino acids, regardless of length or post-translational modification, e.g., glycosylation, phosphorylation, acetylation or nitrosylation.

By the terms "ΔFosB," "ΔFosB protein," and "DeltaFosB" is meant the protein encoded by the ΔFosB gene, which is an alternative splicing product of the fosB gene, that is described in Nakabeppu et al. (Cell 64, 751-759 (1991)), and that displays a functional activity of a native ΔFosB protein. ΔFosB is a transcription factor. A "functional activity" of a protein is any activity associated with the physiological function of the protein. For example, functional activities of a native ΔFosB protein may include: e.g., regulation of genes for dynorphin, AMPA receptor subunit GluR2, $NF_{\kappa}B$, and CDK5. It is involved in L-dopa induced dyskinesia, drug addiction, bone formation and adipogenesis.

"Purified," as used herein, means separated from many other compounds or entities. A compound or entity (e.g., nucleic acid, protein, virus, viral vector) may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%.

The phrases "isolated" or "biologically pure" refer to material which is substantially or essentially free from components which normally accompany it as found in its native state.

As used herein, the phrases "decreased ΔFosB expression", "inhibition of ΔFosB expression" and "downregulated ΔFosB expression" are used interchangeably to mean decreased levels of ΔFosB mRNA and protein expression as compared to normal levels or normal tissues.

By the term "gene" is meant a nucleic acid molecule that codes for a particular protein, or in certain cases, a functional or structural RNA (ribonucleic acid) molecule.

As used herein, a "nucleic acid" or a "nucleic acid molecule" means a chain of two or more nucleotides such as RNA and DNA (deoxyribonucleic acid).

As used herein, the phrase "expression control sequence" refers to a nucleic acid that regulates the replication, transcription and translation of a coding sequence in a recipient cell. Examples of expression control sequences include promoter sequences, polyadenylation (pA) signals, introns, transcription termination sequences, enhancers, upstream regulatory domains, origins of replication, and internal ribosome entry sites ("IRES"). The term "promoter" is used herein to refer to a DNA regulatory sequence to which RNA polymerase binds, initiating transcription of a downstream (3' direction) coding sequence.

As used herein, the terms "operable linkage" and "operably linked" refers to a physical or functional juxtaposition of the components so described as to permit them to function in their intended manner. In the example of an expression control element in operable linkage with a nucleic acid, the relationship is such that the control element modulates expression of the nucleic acid.

By the terms "ΔFosB gene," "ΔFosB polynucleotide," and "ΔFosB nucleic acid" is meant a native human ΔFosB-encoding nucleic acid sequence, e.g., the native human ΔFosB gene (SEQ ID NO:3), a nucleic acid having sequences from which a ΔFosB cDNA can be transcribed; and/or allelic variants and homologs of the foregoing. The terms encompass double-stranded DNA, single-stranded DNA, and RNA. ΔFosB is the truncated splice variant of FosB.

Human ΔFosB Nucleic Acid Sequence:

(SEQ ID NO: 3)

```
ATGTTTCAGGCTTTCCCCGGAGACTACGACTCCGGCTCCCGGTGCAGCTC
CTCACCCTCTGCCGAGTCTCAATATCTGTCTTCGGTGGACTCCTTCGGCA
GTCCACCCACCGCCGCCGCCTCCCAGGAGTGCGCCGGTCTCGGGGAAATG
CCCGGTTCCTTCGTGCCCACGGTCACCGCGATCACAACCAGCCAGGACCT
CCAGTGGCTTGTGCAACCCACCCTCATCTCTTCCATGGCCCAGTCCCAGG
GGCAGCCACTGGCCTCCCAGCCCCCGGTCGTCGACCCCTACGACATGCCG
GGAACCAGCTACTCCACACCAGGCATGAGTGGCTACAGCAGTGGCGGAGC
GAGTGGCAGTGGTGGGCCTTCCACCAGCGGAACTACCAGTGGGCCTGGGC
CTGCCCGCCCAGCCCGAGCCCGGCCTAGGAGACCCCGAGAGGAGACGCTC
ACCCCAGAGGAAGAGGAGAAGCGAAGGGTGCGCCGGGAACGAAATAAACT
AGCAGCAGCTAAATGCAGGAACCGGCGGAGGGAGCTGACCGACCGACTCC
AGGCGGAGACAGATCAGTTGGAGGAAGAAAAAGCAGAGCTGGAGTCGGAG
ATCGCCGAGCTCCAAAAGGAGAAGGAACGTCTGGAGTTTGTGCTGGTGGC
CCACAAACCGGGCTGCAAGATCCCCTACGAAGAGGGGCCCGGGCCGGGCC
CGCTGGCGGAGTGAAGTTCAAGTCCTCGGCGACCCCTTCCCCGTTGTTAA
CCCTTCGTACACTTCTTCGTTTGTCCTCACCTGCCCGGAGGTCTCCGCGT
TCGCCGGCGCCCAACGCACCAGCGGCAGTGACCAGCCTTCCGATCCCCTG
AACTCGCCCTCCCTCCTCGCTCTGTGA.
```

As used herein, the terms "shRNA" and "short hairpin RNA" mean any artificial RNA molecule with a tight hairpin turn that can be used to silence target gene expression via RNA interference (RNAi). shRNA is encompassed by the terms "interfering RNA" and "RNA interference molecule." Methods of designing and using shRNA for gene therapy applications are known in the art, e.g., U.S. Patent Applications Pub. Nos. 2019/0282639 and 2019/0256858; Scarborough R. J. & Gatignol A., Viruses 2018 vol. 10:1-19; DiGiusto et al., Sci. Transl. Med. 2010 vol. 2:1-18; Wang et al., PLoS ONE 2013 vol. 8; Bofill-De Ros X & Gu S., Methods 2016 vol. 103:157-166; etc., all incorporated herein by reference.

A "vector" includes a composition of matter which can be used to deliver a nucleic acid (e.g., DNA, RNA) of interest to the interior of a cell, including a nucleic acid molecule capable of transporting another nucleic acid to which it has been linked. Numerous vectors are known in the art including, but not limited to, linear polynucleotides, polynucleotides associated with ionic or amphiphilic compounds, plasmids, liposomes, cationic lipids, cationic polymers, inorganic nanoparticles, and viruses (viral vectors). Thus, the term "vector" includes an autonomously replicating plasmid or a virus. Examples of viral vectors include, but are not limited to, AAV vectors, retroviral vectors, lentiviral vectors, adenoviral vectors, and the like. An expression construct can be replicated in a living cell, or it can be made synthetically. Vectors capable of directing the expression of genes to which they are operatively linked are often referred to as "expression vectors." For purposes of this application, the terms "expression construct," "expression vector," and "vector," are used interchangeably to demonstrate the application of the invention in a general, illustrative sense, and are not intended to limit the invention.

A recombinant "viral vector" is derived from the wild type genome of a virus (e.g., AAV, lentivirus), by using molecular methods to remove the wild type genome from the virus, and replacing it with a non-native nucleic acid, such as a heterologous polynucleotide sequence (e.g., a therapeutic gene or other therapeutic nucleic acid expression cassette). A "recombinant lentivirus vector" or "recombinant lentiviral vector" is derived from the wild type genome of a lentivirus (e.g., the human immunodeficiency virus). A "recombinant AAV vector" or "rAAV vector" or "rAAV vector genome" is derived from the wild type genome of AAV. Typically, for AAV, one or both inverted terminal repeat (ITR) sequences of the wild type AAV genome are retained in the rAAV vector. A recombinant viral vector (e.g., rAAV vector) sequence can be packaged into a virus (also referred to herein as a "particle" or "virion") for subsequent infection (transformation) of a cell, ex vivo, in vitro or in vivo. Where a rAAV vector sequence is encapsidated or packaged into an AAV particle, the particle can be referred to as a "rAAV." Such particles or virions include proteins that encapsidate or package the vector genome. Particular examples include viral envelope proteins, and in the case of AAV, capsid proteins (VP1, VP2, VP3).

AAV capsid proteins of any suitable serotype (e.g., serotypes AAV1, AAV2, AAV3, AAV4, AAV5, AAV6, AAV7, AAV8, AAV9, AAV10, AAV11, AAV12, etc.) can be used in the rAAV described herein. Currently, there are more than 100 AAV serotypes identified that differ in the binding capacity of capsid proteins to specific cell surface receptors that can transduce different cell types and brain regions in the central nervous system (CNS). As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Recombinant vectors (e.g., rAAV vectors or plasmids), recombinant viruses or virions (recombinant viral particles), as well as methods and uses thereof, include any viral strain or serotype. A rAAV vector can be based upon an AAV serotype genome distinct from one or more of the capsid proteins that package the vector (i.e., pseudotyped). rAAV (particles) including rAAV vectors (e.g., recombinant viral genomes) can include at least one capsid protein from a different serotype, a mixture of serotypes, or hybrids or chimeras of different serotypes, such as a VP1, VP2 or VP3 capsid protein of AAV1, AAV2, AAV3, AAV4, AAV5, AAV6, AAV7, AAV8, AAV9, AAV10, AAV11, AAV12, or AAV13. In gene therapy applications, commonly a pseudotyped rAAV includes ITRs of wildtype AAV2 and capsid proteins from a different serotype or serotypes. In the experiments described herein, the rAAV tested (rAAV-ΔFosB shRNA-GFP) included an rAAV vector having replication protein from serotype AAV2 and AAV capsid proteins from serotype AAV5.

The terms "loop" and "loop sequence" mean any nucleic acid that is of a sufficient length to permit the antisense and sense sequences to anneal and form a double-stranded structure (or stem). One example of a loop sequence present in some embodiments of vectors as described herein is the sequence TTCAAGAGA. In a typical embodiment of a recombinant viral vector as described herein, the heterologous polynucleotide sequence comprises DNA sequences, and once inside the target cell, the DNA sequences are transcribed into shRNA sense and antisense sequences separated by a loop sequence, resulting in a double-stranded RNA hairpin.

The terms "patient," "subject" and "individual" are used interchangeably herein, and mean a mammalian (e.g., human) subject to be treated, diagnosed, and/or to obtain a biological sample from. Typically, the subject is affected with PD and dyskinesia (e.g., LID).

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der waals).

The term "labeled," with regard to a nucleic acid, peptide, polypeptide, cell, virus, probe or antibody, is intended to encompass direct labeling of the nucleic acid, peptide, polypeptide, cell, virus, probe or antibody by coupling (i.e., physically linking) a detectable substance to the nucleic acid, peptide, polypeptide, cell, virus, probe or antibody.

When referring to a nucleic acid molecule or polypeptide, the term "native" refers to a naturally-occurring (e.g., a wild type (WT)) nucleic acid or polypeptide.

As used herein, the term "therapeutic agent" is meant to encompass any molecule, chemical entity, composition, drug, or biological agent capable of curing, healing, alleviating, relieving, altering, remedying, ameliorating, improving or affecting a disease, the symptoms of disease, or the predisposition toward disease. The term "therapeutic agent" includes shRNA, small molecules, antisense reagents, nucleic acids, siRNA, antibodies, enzymes, polypeptides, peptides, recombinant viruses, recombinant viral vectors, organic or inorganic molecules, natural or synthetic compounds and the like.

As used herein, the terms "treatment" and "therapy" are defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease. Methods and uses of the compositions, vectors and viruses described herein include treatment methods, which result in any therapeutic or beneficial effect. In particular aspects of the methods and uses of the compositions, vectors and viruses disclosed herein, expression of the nucleic acid provides a therapeutic benefit to the mammal (e.g., human suffering from PD). In various embodiments, further included are inhibiting, decreasing or reducing one or more adverse (e.g., physical) symptoms, disorders, illnesses, diseases or complications caused by or associated with a disease (e.g., LID associated with PD).

By the phrases "therapeutically effective amount" and "effective dosage" is meant an amount sufficient to produce a therapeutically (e.g., clinically) desirable result; for example, the result can be decreasing ΔFosB expression or activity in a cell, treating dyskinesia in a subject (e.g., mammals including humans), decreasing AIMs in a subject suffering from PD and dyskinesia, etc.

As used herein, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity can be measured using any appropriate sequence analysis software.

ΔFosB is highly conserved. The shRNA targeting sequence identified and targeted in the experiments described herein has only one base pair difference among rat, human and monkey as shown below in Table 1.

Table 1: Alignment of the ΔFosB shRNA targeting sequence among rat, human and monkey. Human and monkey have the same shRNA targeting sequence, which has one base pair difference compared to the rat.

```
Rat shRNA targeting sequence
                                        (SEQ ID NO: 1)
CUGGCCGAGUGAAGUUCAA

Human corresponding sequence
                                        (SEQ ID NO: 4)
CUGGCGGAGUGAAGUUCAA

Monkey corresponding sequence
                                        (SEQ ID NO: 4)
CUGGCGGAGUGAAGUUCAA
```

When referring to mutations in a nucleic acid molecule, "silent" changes are those that substitute one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with another amino acid having similar characteristics.

Although compositions, vectors, viruses, kits, and methods similar or equivalent to those described herein can be used in the practice or testing of the present invention, suitable compositions, vectors, viruses, kits, and methods are described below. All publications, patent applications, patents and other references such as GenBank citations (accession numbers) and ATCC citations mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 3A: Rats with striatal injection of AAV-sh[NT] began to develop mild AIMs from Day 1 and showed continuous increase of AIMs score after Day 4, while rats injected with AAV-sh[ΔFosB] continued to exhibit lower AIMs scores during the successive 18 days. FIGS. 3B and 3C: There was no significant difference in total (FIG. 3B) and peak (FIG. 3C) numbers of rotation in response to L-Dopa administration between the two groups of rats. Data are mean±SEM. *p<0.05, versus control rats (scrambled).

FIG. 4A: ΔFosB lacks the C-terminal 101 amino acids of FosB as a result of alternative splicing causing frame shift that introduces the termination codon 'UGA' in its mRNA (indicated as '*'). In FIG. 4A, SEQ ID NO: 5 is the top sequence and includes the deleted sequence fragment shown in the top box; below it is SEQ ID NO: 6, which is the ΔFosB specific region targeted for siRNA design. FIG. 4B shows siRNA targeting sequences of siRNA #1, siRNA #2 and siRNA #3. Also in FIG. 4B, double stranded siRNAs (sense and antisense strands) corresponding to the target sequences and a control non-targeting (NT) siRNA were synthesized and evaluated by transient transfection of rat PC12 cells followed by Western blot analysis. siRNA #1 had the best knockdown effect. The three rat nucleic acid sequences in FIG. 4B from top to bottom are: SEQ ID NO: 1, SEQ ID NO: 7 AND SEQ ID NO: 8. siRNA #1 sense strand is CUGGCCGAGUGAAGUUCAAdTdT (SEQ ID NO: 9), antisense strand is UUGAACUUCACUCGGCCAGdTdT (SEQ ID NO: 10); siRNA #2 sense strand is CGCUGGCCGAGUGAAGUUCdTdT (SEQ ID NO: 11), antisense strand is GAACUUCACUCGGCCAGCGdTdT (SEQ ID NO: 12); and siRNA #3 sense strand is CCGCUGGCCGAGUGAAGUUdTdT (SEQ ID NO: 13), antisense strand is AACUUCACUCGGCCAGCGGdTdT (SEQ ID NO: 14). FIG. 4C: ΔFosB shRNA (shRNA #1: sense strand is SEQ ID NO: 1, antisense strand is SEQ ID NO: 2) was designed based on siRNA #1 sequence (SEQ ID NO: 9). DNA sequence corresponding to shRNA #1 in sense CTGGCCGAGTGAAGTTCAA (SEQ ID NO: 15) and antisense TTGAACTTCACTCGGCCAG (SEQ ID NO: 16) orientations, separated by a loop sequence (TTCAAGAGA), was cloned into a rAAV2/5 cis vector, such that the resulting RNA hairpin (shRNA #1) was under transcriptional control of the U6 promoter with GFP co-expression driven by the CMV promoter. The control vector AAV-sh[NT] is isogenic to AAV-sh[ΔFosB], except that it expresses a nontargeting shRNA instead of shRNA #1. ITR=inverted terminal repeat; pA=poly(A) tail. FIGS. 4D, 4**E: In vivo shRNA transfer in the rat striatum detected by GFP expression. Scale bar=100 nm.

FIG. 6A: The use of the right (impaired) paw compared to total wall touches was similar between the two groups of rats (rAAV-shRNA ΔFosB and rAAV-scrambled shRNA) before L-Dopa/benserazide injection. After L-Dopa/benserazide injection, the use of the right paw recovered to almost 50% in both rat groups. FIG. 6B: Initiation time (sec) measured before L-Dopa/benserazide injection shows that rats in both groups could not move their right forelimbs for almost 180 s, which is a break-off point. Following L-Dopa/benserazide injection, initiation time was shortened similarly (below 20 s) in both rat groups (p>0.05). (C-F) Step counts for the right (impaired, FIG. 6C and FIG. 6D) and left (intact, FIG. 6E and FIG. 6F) forelimbs in the forward (Fw) and backward (Bw) directions, pre (FIG. 6C and FIG. 6E) and post (FIG. 6D and FIG. 6F) L-Dopa/benserazide injection. For the right (impaired) forelimb, the step counts in both Fw and Bw directions increased after L-Dopa injection in both groups (from ~5 before L-Dopa injection to 10-15 after injection). For the left (intact) forelimb, the step counts remained the same before and after the injection (12 to 15 in each direction; p>0.05).

FIG. 7A: The use of the impaired paw was similar between the two groups of rats before L-Dopa/benserazide injection. After L-Dopa/benserazide injection, the deficit of the right paw recovered to almost 50% in both rat groups. FIG. 7B: Initiation times measured before L-Dopa/benserazide injection (170 to 180 s) in both groups, shortened similarly after L-Dopa/benserazide injection (below 20 s) in both rat groups (p>0.05). (FIGS. 7C-7F) Step counts for the right (impaired, FIGS. 7C and 7D) and left (intact, FIGS. 7E and 7F) forelimbs in the forward (Fw) and backward (Bw) directions, pre (FIGS. 7C and 7E) and post (FIGS. 7D and 7F) L-Dopa/benserazide injection. For the right (impaired) forelimb, the step counts in both Fw and Bw directions increased after L-Dopa injection in both groups (from ~5 before L-Dopa injection to 10-15 after injection). For the left (intact) forelimb, the step counts remained the same before and after the injection (10 to 12 in each direction; p>0.05).

FIG. 8A: Western blot analyses of striatal tissue lysates for the indicated proteins. Each lane represents striatal tissue lysate from a separate animal. FIG. 8B: Quantification of indicated band intensities relative to (β-actin in FIG. 8A. Data represent means±standard error of the mean: *p<0.001 (unpaired t-tests).

(FIGS. 9A-9D) NeuN (neuronal marker) staining in the striatal tissues of rats injected AAV-sh[NT] (FIGS. 9A, 9B) and AAV-sh[ΔFosB] (FIGS. 9C, 9D) showed there was no apparent loss of striatal neurons caused by viral injection in both groups. Panels of FIG. 9B and FIG. 9D are high magnification of squares in FIG. 9A and FIG. 9C, respectively. FIGS. 9E-9H: By immunohistochemistry for GFAP (a marker of astrocyte, FIG. 9E and FIG. 9F) or Iba-1 (a marker of microglia, FIG. 9G and FIG. 9H), neither active astrocytes nor microglial infiltration were observed in the striatum of rats in both groups. Scale bar in FIG. 9A represents 100 μm (FIG. 9A and FIG. 9C) and 40 μm (FIG. 9B and FIGS. 9D-9H).

DETAILED DESCRIPTION

Figure 4A:
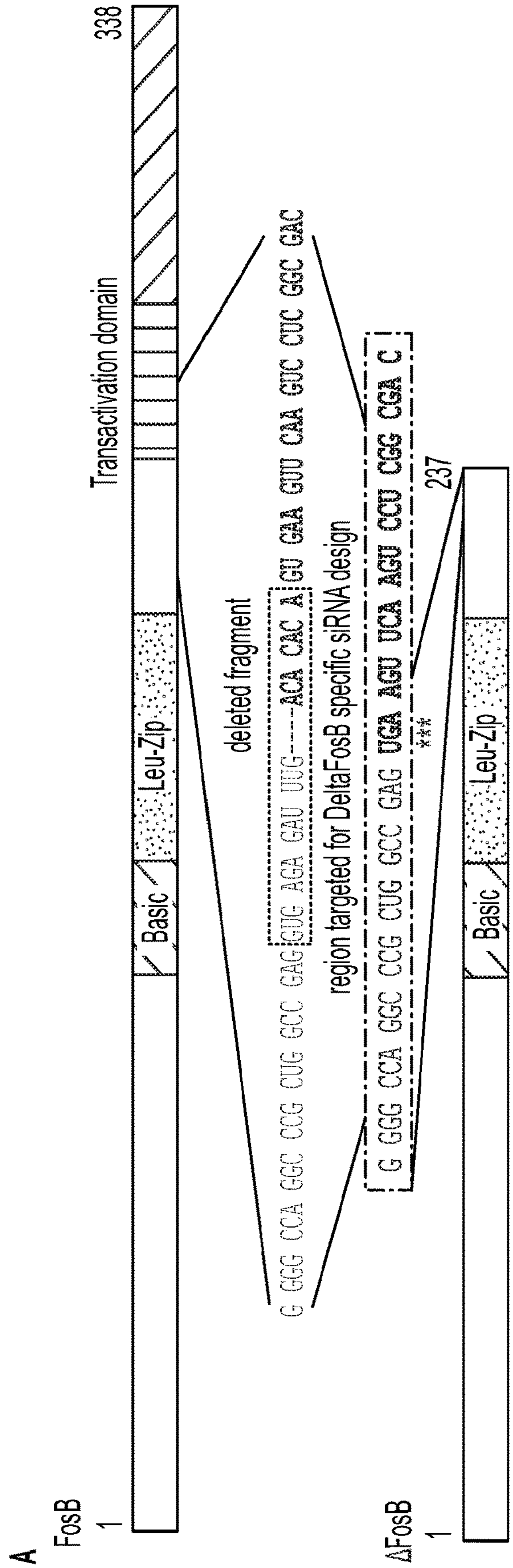
FIGS. 4A, 4B, 4C, 4D, and 4E illustrate generation of a viral vector targeting specifically ΔFosB in vivo in rats.
Figure 4B:
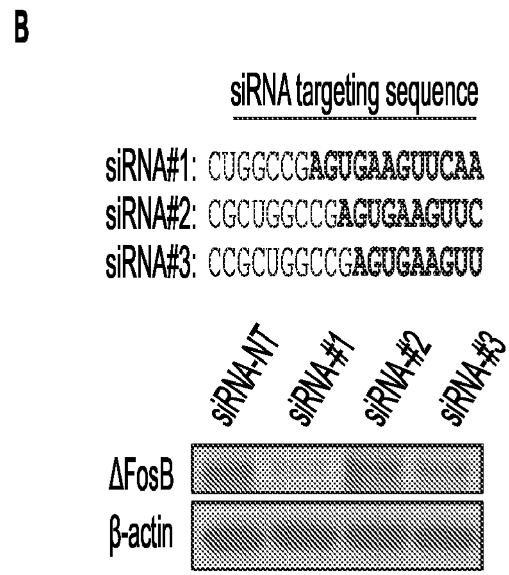
Figure 4C:
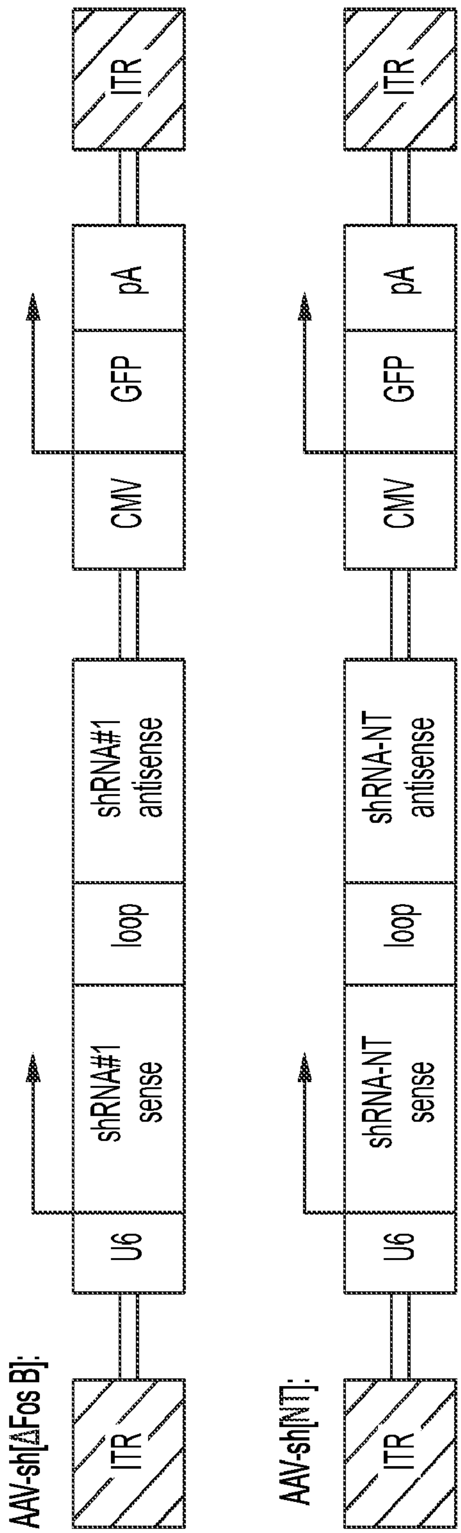
Figure 5:
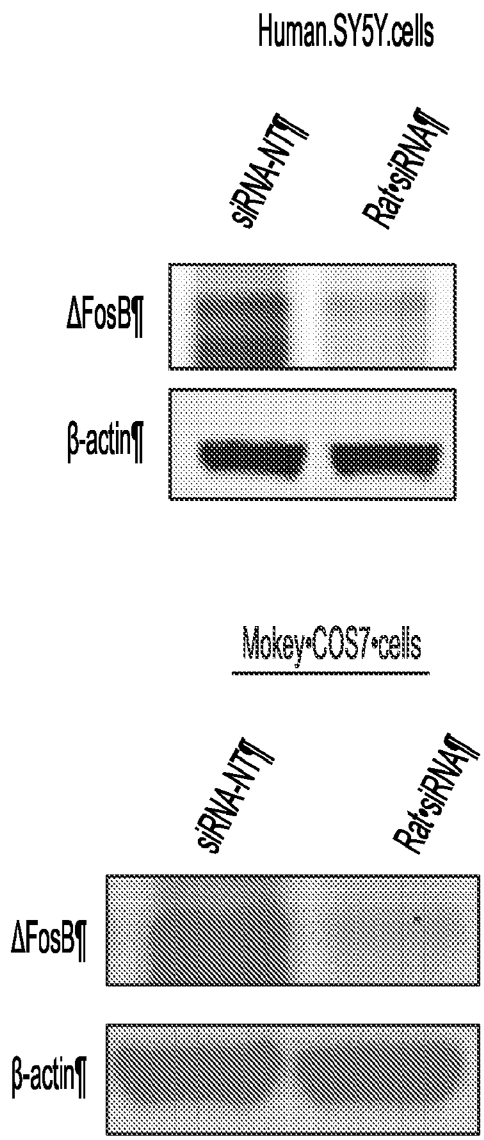
FIG. 5 is a pair of Western blots showing that the rat ΔFosB shRNA as described herein down-regulates ΔFosB protein expression in human and monkey cells.
Figure 6A:
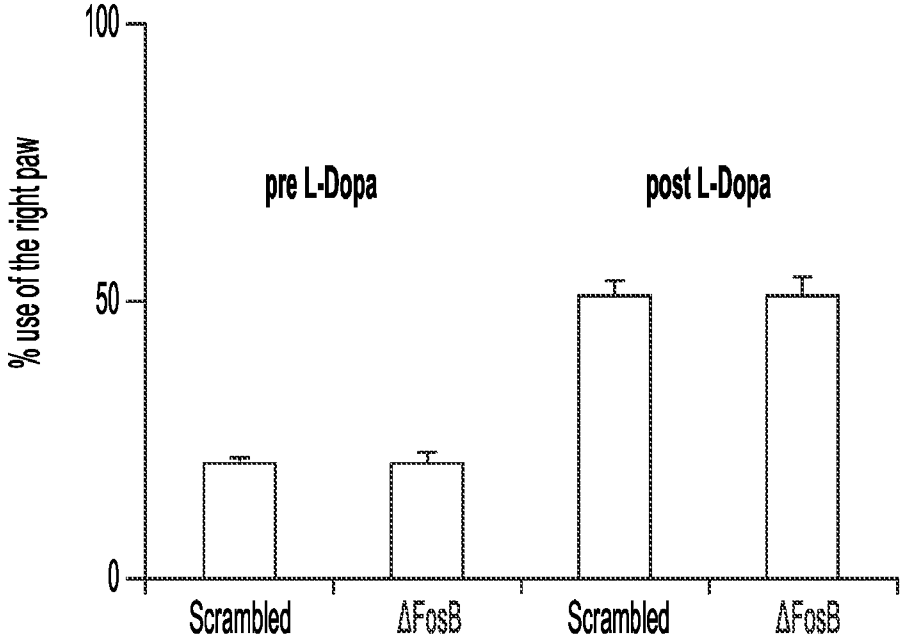
FIGS. 6A, 6B, 6C, 6D, 6E and 6F are a series of graphs showing that knockdown of ΔFosB using AAV-sh[ΔFosB] did not alter the basal parkinsonism induced by 6-OHDA lesion or the baseline beneficial effects of L-Dopa. Cylinder test (FIG. 6A), initiation time (FIG. 6B), and adjusting steps (FIGS. 6C-6F) performed before and after i.p. injection of L-Dopa (12 mg/kg) plus benserazide (12 mg/kg) before initiating daily treatment (day 7).
Figure 6B:
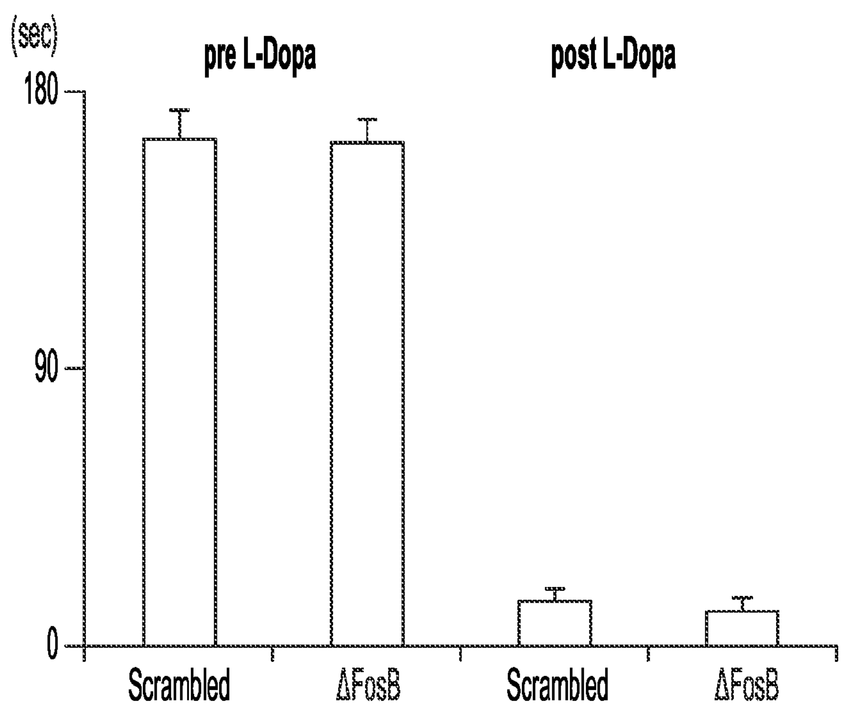
Figure 6C:
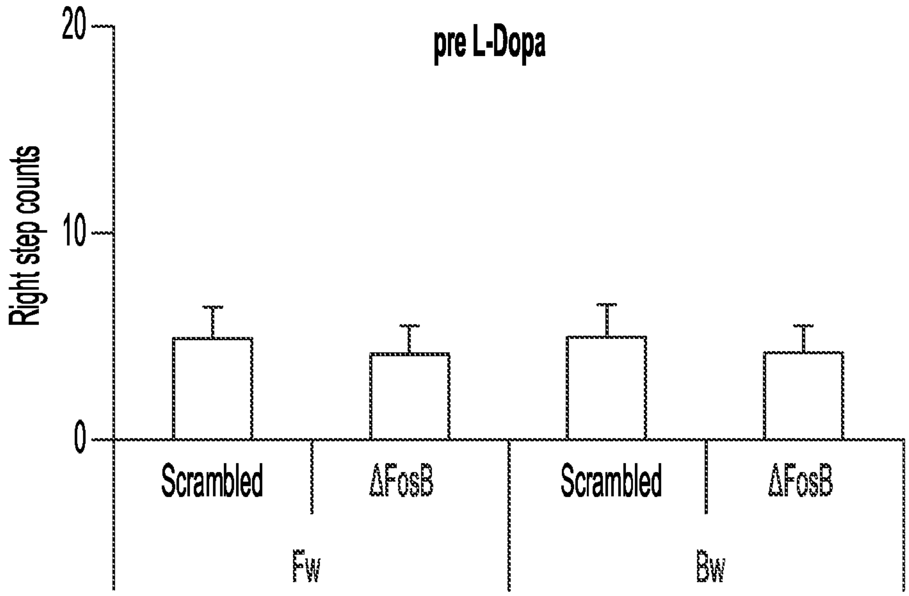
Figure 6D:
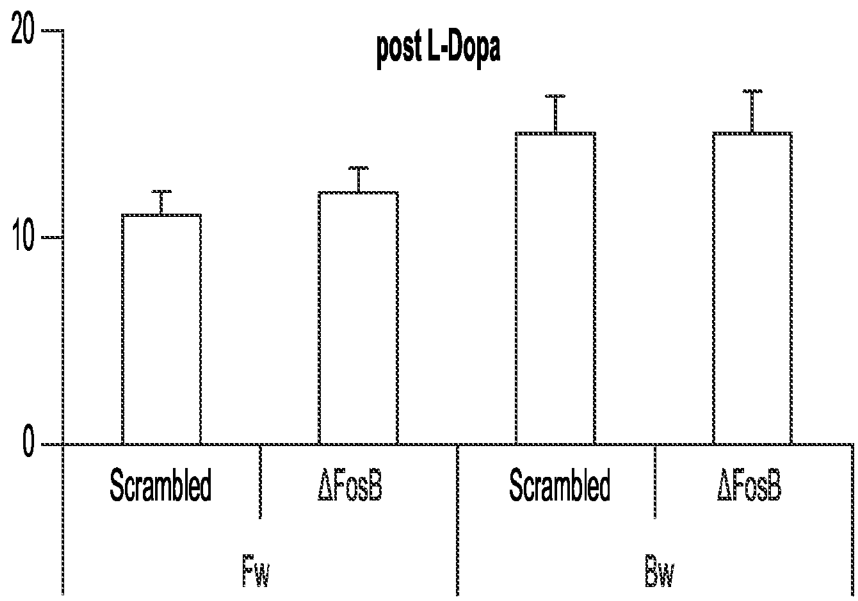
Figure 6E:
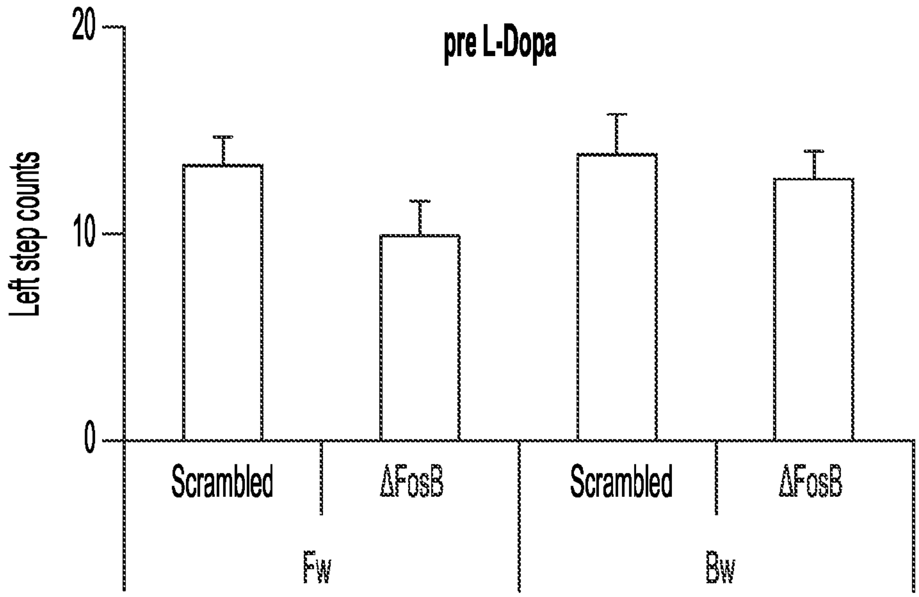
Figure 6F:
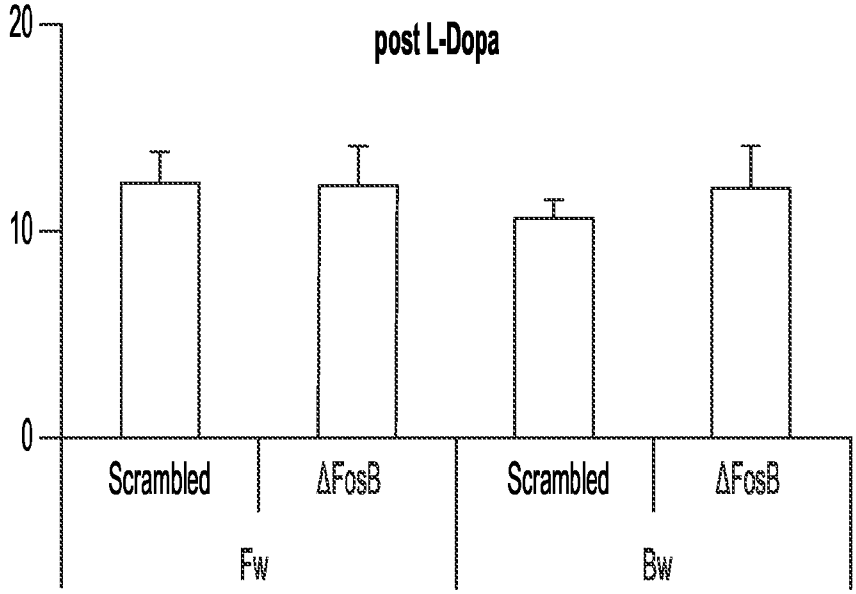

Described herein are compositions, vectors, viruses, and kits including a nucleic acid encoding a shRNA specific for (targeting) ΔFosB for decreasing ΔFosB expression in a cell, and treating dyskinesia (e.g., LID) in a subject (e.g., human suffering from PD). Methods of using these compositions, vectors, viruses, and kits including these compositions, vectors, and viruses are also described herein. The experimental results described herein demonstrate the therapeutic utility of an inhibitor of ΔFosB expression for reducing ΔFosB expression, and attenuating AIMs. All known antisense molecules target both FosB and ΔFosB (FosB/ΔFosB). Because ΔFosB is the product of alternative splicing of FosB, only the junction sequence after splicing can be used to design siRNA that targets specifically ΔFosB. The novel ΔFosB shRNA sequences described herein are the first to target specifically ΔFosB (see FIG. 4A, 4B) due to the design of the ΔFosB shRNA based on the junction sequence, which confers specificity for ΔFosB. Additionally, ΔFosB is highly conserved. The sequence identified here for targeting with shRNA and shown in FIG. 4A has only one base pair difference among rat, human and monkey (Table 1). This sequence homology makes it possible to target human and monkey ΔFosB using rat shRNA sequence. As shown in FIG. 5, rat shRNA is also highly effective in reducing ΔFosB protein level in human SH-SY5Y cells and monkey COST cells. This indicates that the shRNA sequences and vectors described herein are also effective in reducing ΔFosB in humans.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; The Condensed Protocols From Molecular Cloning: A Laboratory Manual, by Joseph Sambrook et al., Cold Spring Harbor Laboratory Press, Cold Spring Harbor, N.Y., 2006; and Current Protocols in Molecular Biology, ed. Ausubel et al., Greene Publishing and Wiley-Interscience, New York, 1995 (with periodic updates). Conventional methods of gene transfer and gene therapy may also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; Viral Vectors for Gene Therapy: Methods and Protocols, ed. Otto-Wilhelm Merten and Mohammed Al-Rubeai, Humana Press, 2011; and Nonviral Vectors for Gene Therapy: Methods and Protocols, ed. Mark A. Findeis, Humana Press, 2010. Methods for constructing and using viral vectors are known in the art (see, e.g., Miller and Rosman, BioTechniques 1992, 7:980-990). Methods for large-scale production of rAAV are described in Urabe M. J. (2006) Virol. 80:1874-1885; Kotin R. M. (2011) Hum. Mol. Genet. 20:R2-6; Kohlbrenner E. et al. (2005) Mol. Ther. 12:1217-1225; and Mietzsch M. (2014) Hum. Gene Ther. 25:212-222. For a review of rAAV gene therapy methods, see Samulski, R. J. and Muzyczka, N. (2014) AAV-Mediated Gene Therapy for Research and Therapeutic Purposes, Annu. Rev. Virol. 1:427-451. Use of rAAV for gene delivery into the CNS is described in Hammond et al., PLoS One vol. 12(12): p. 1-22, 2017. rAAV vectors, variants, chimeras, and rAAV vector mediated gene transfer methods are described in U.S. Pat. No. 9,840,719.

Vectors, Viruses and Compositions for Reducing ΔFosB Expression and Activity and Treating Dyskinesia Typically, a recombinant viral vector (e.g., rAAV vector) as described herein includes (a) a heterologous polynucleotide sequence that includes a nucleic acid sequence encoding a shRNA specific for ΔFosB, and (b) ITRs flanking the heterologous polynucleotide sequence. By "specific for ΔFosB" is meant the shRNA targets ΔFosB. As shown in FIG. 4A, the target mRNA sequence of ΔFosB is GGGGCCAGGCCCGCUGGCCGAGUGAAGUUCAA-GUCCUCGGCGAC (SEQ ID NO: 6); accordingly, a shRNA that targets ΔFosB includes an antisense sequence that is complementary to the ΔFosB target sequence and a sense sequence that is the reverse complement of the antisense sequence. In a shRNA, the sense and antisense sequences are typically separated by a spacer or loop sequence (e.g., TTCAAGAGA). A spacer or loop can be of a sufficient length to permit the antisense and sense sequences to anneal and form a double-stranded structure (or stem). In a typical recombinant viral vector (e.g., rAAV vector), the shRNA has at least 90% or more sequence identity with a sense strand of sequence SEQ ID NO: 1 (e.g., an shRNA including SEQ ID NO: 4) and/or at least 90% or more sequence identity with SEQ ID NO: 1's antisense strand, i.e., the sequence of SEQ ID NO:2 (e.g., SEQ ID NO: 23—the antisense strand of SEQ ID NO: 4). In embodiments, the shRNA includes a shRNA having at least 85% sequence identity with one or both of SEQ ID NOs: 1-2 (e.g., an shRNA including SEQ ID NO: 4 and the antisense strand of SEQ ID NO: 4). In embodiments, the shRNA includes a shRNA having at least 90% sequence identity with one or both of SEQ ID NOs: 1-2. In embodiments, the shRNA includes a shRNA having at least 95% sequence identity with one or both of SEQ ID NOs: 1-2. In embodiments, the shRNA includes an shRNA including SEQ ID NO: 4 and the antisense strand of SEQ ID NO: 4 (i.e., the sequence of SEQ ID NO: 23). In some embodiments, a recombinant viral vector (e.g., an rAAV vector) as described herein is present within recombinant virus (e.g., rAAV particles). In the experiments described below, a rAAV includes a rAAV vector having replication proteins from serotype AAV2 and AAV capsid proteins from serotype AAV5.

In addition to shRNA having at least 80% sequence identity with one or both of SEQ ID NOs: 1-2, shRNA having at least 80% (e.g., 80%, 85%, 90%, 95%) sequence identity with a sense strand of CGCUGGCCGAGUGAAGUUC (SEQ ID NO: 7) which corresponds to siRNA #2, an antisense strand of GAAC-UUCACUCGGCCAGCG (SEQ ID NO: 17) which is the antisense of SEQ ID NO: 7, a sense strand of CCGCUGGCCGAGUGAAGUU (SEQ ID NO: 8) which corresponds to siRNA #3, and/or an antisense strand of AACUUCACUCGGCCAGCGG (SEQ ID NO: 18) which is the antisense of SEQ ID NO: 8, can be included in the recombinant viral vectors (e.g., rAAV vectors, recombinant lentiviral vectors) and recombinant viruses (e.g., rAAV, recombinant lentiviruses) described herein.

Compositions described herein for reducing ΔFosB expression and/or activity and treating dyskinesia in a subject include a therapeutically effective amount of a recombinant viral vector (e.g., an rAAV vector, a recombinant lentivirus vector) or recombinant virus (e.g., rAAV, recombinant lentivirus) as described herein. In some embodiments, a therapeutically effective amount is an amount effective for reducing ΔFosB expression in cells of the subject and decreasing or eliminating AIMS in the subject. The compositions can also include a pharmaceutically acceptable carrier. Reducing ΔFosB expression includes reducing ΔFosB transcription and inhibiting processing of ΔFosB RNAs. Reducing ΔFosB activity includes reducing the effect of ΔFosB on ΔFosB target genes involved in the cellular/circuit signaling generating LID.

The shRNA specific for ΔFosB is in some embodiments contained within an expression vector, non-viral vector, or a viral vector. The vectors may be episomal, e.g., plasmids, virus-derived vectors, or may be integrated into the target cell genome, through homologous recombination or random integration. Viruses are naturally evolved vehicles which efficiently deliver their genes into host cells and therefore are desirable vector systems for the delivery of therapeutic nucleic acids. Preferred viral vectors exhibit low toxicity to the host cell and produce/deliver therapeutic quantities of the nucleic acid of interest (in some embodiments, in a tissue-specific manner). A number of viral based systems have been developed for gene transfer into mammalian cells. For example, AAV provides a convenient platform for gene delivery systems. As another example, retroviruses (e.g., lentiviruses) provide a convenient platform for gene delivery systems. Any suitable type of lentivirus may be used. In a typical embodiment, a third-generation, self-inactivating (SIN) lentiviral vector is used. Construction, large-scale manufacturing, and clinical use of third-generation SIN lentiviral vectors are well known in the art. In yet other examples, adenovirus vectors, retrovirus vectors, herpesvirus vectors, alphavirus vectors, or lentivirus vectors are used. A selected nucleic acid sequence can be inserted into a vector (a vector genome) and packaged in viral particles using techniques known in the art (e.g., an rAAV vector packaged in rAAV particles, a recombinant lentivirus vector packaged within recombinant lentivirus particles). The recombinant virus can then be isolated and delivered to cells of the subject.

In the experiments described herein, ΔFosB expression was reduced using shRNA specific for (targeting) ΔFosB, and in these experiments, a nucleic acid sequence encoding the shRNA specific for ΔFosB was contained within a rAAV vector. Any suitable rAAV vector can be used. Recombinant AAV vectors include AAV1, AAV2, AAV3, AAV4, AAV5, AAV6, AAV7, AAV8, AAV9, AAV10, AAV11, AAV12, AAV13, and variants thereof. Examples of rAAV can include capsid sequence of any of AAV1, AAV2, AAV3, AAV4, AAV5, AAV6, AAV7, AAV8, AAV9, AAV10, AAV11, AAV12, AAV13, or a capsid variant of AAV1, AAV2, AAV3, AAV4, AAV5, AAV6, AAV7, AAV8, AAV9, AAV10, AAV11, AAV12, AAV13. Particular capsid variants include capsid variants of AAV1, AAV2, AAV3, AAV4, AAV5, AAV6, AAV7, AAV8, AAV9, AAV10, AAV11, AAV12, AAV13, such as a capsid sequence with an amino acid substitution, deletion or insertion/addition. AAV vectors can include additional elements that function in cis or in trans. In particular embodiments, an rAAV vector that includes a vector genome also has: one or more inverted terminal repeat (ITR) sequences that flank the 5' or 3' terminus of the nucleic acid sequence encoding shRNA specific for ΔFosB; an expression control element that drives transcription (e.g., a promoter or enhancer) of the nucleic acid sequence, such as a constitutive or regulatable control element, or tissue-specific expression control element; and/or a poly-Adenine sequence located 3' of the nucleic acid sequence. In a typical embodiment, an AAV serotype having CNS (e.g., neuronal) tropism is used. For example, in humans, AAV9 and AAV2/1 (pseudotyped AAV2 vector encapsidated by AAV1 capsid proteins), AAV1, AAV2, AAV4, AAV5, AAV8, AAV9 have high neuronal tropism (for reviews of in vivo tissue tropisms, see Hammond et al., PLoS One vol. 12(12): p. 1-22, 2017; Nonnenmacher M. and Weber T. (2012) Gene Ther. 19:649-658; Agbandje-McKenna M. and Kleinschmidt J. (2011) AAV capsid and cell interactions—In Adeno-Associated Virus: Methods and Protocols, ed. R O Snyder, P Moullier, p. 47-92, Humana Press, Clifton, NJ; Asokan A. et al. (2012) Mol. Ther. 4:699-708; and Haery L, Deverman B E, Matho K S, et al. Adeno-Associated Virus Technologies and Methods for Targeted Neuronal Manipulation. Front Neuroanat. 2019; 13:93). In some embodiments, AAV8 and AAV9 can be used.

Methods are well known in the art for generating rAAV vectors and rAAV (virions/particles) having improved features for delivering therapeutic agents. rAAV having new capsid variants that, for example, have higher transduction frequency or increased neuronal tropism, can be used. For example, capsid libraries can be screened in a process called directed evolution (Bartel M. A. (2012) Gene Ther. 19:694-700) to select capsids enriched for infecting a particular tissue or cell type. As another example, rAAV having capsids decorated with ligand targeted to a specific cell type (e.g., striatal neuron-specific) can be used. As another example, pseudotyped rAAV (nucleic acid or genome derived from a first AAV serotype that is encapsidated or packaged by an AAV capsid containing at least one AAV Cap protein of a second serotype (i.e., one different from the first AAV serotype)) can be used. In addition to capsid modifications, rAAV as described herein may include tissue-specific promoters (e.g., neuron-specific promoters) and inducible promoters. For a review of rAAV gene therapy methods, see Samulski, R. J. and Muzyczka, N. (2014) AAV-Mediated Gene Therapy for Research and Therapeutic Purposes, Annu. Rev. Virol. 1:427-451. rAAV, variants, chimeras, and rAAV-mediated gene transfer methods are also described in U.S. Pat. No. 9,840,719.

rAAV can be produced using any suitable methods. Methods for large-scale production of rAAV are known and are described in Urabe M. J. (2006) Virol. 80:1874-1885; Kotin R. M. (2011) Hum. Mol. Genet. 20:R2-6; Kohlbrenner E. et al. (2005) Mol. Ther. 12:1217-1225; Mietzsch M. (2014) Hum. Gene Ther. 25:212-222; and U.S. Pat. Nos. 6,436,392, 7,241,447, and 8,236,557. For the experiments described herein, rAAV serotype 2 Rep and rAAV serotype 5 VP1 were cloned to a promoterless vector to obtain pRep2/Cap5 trans construct. shRNA was design based on ΔFosB target region sequence by adding restrictions and a loop. Then the shRNA oligonucleotides were synthesized and cloned to a rAAV cis vector under U6 promoter with GFP co-expression under CMV promoter. To generate AAV2/5 viral particles, rAAV is packaged via a help-free system via rAAV cis and trans plasmids co-transfection into HEK293T cells. Three days post transfection, the rAAV is harvested via three cycles of freeze/thaw of cell pellet. Then the supernatant is loaded to CsCl ultracentrifugation. After ultracentrifugation, the rAAV band is collected at 1.4 g/mL followed by buffer exchange. rAAV titration is determined via qPCR.

The vectors described herein typically include one or more expression control elements. Expression control elements include ubiquitous or promiscuous promoters/enhancers which are capable of driving expression of a polynucleotide (nucleic acid) in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature, the SV40 promoter, the dihydrofolate reductase (DHFR) promoter, the cytoplasmic β-actin promoter, the phosphoglycerol kinase (PGK) promoter, etc.

Expression control elements include those active in a particular tissue or cell type, referred to herein as a "tissue-specific expression control elements/promoters." Tissue-specific expression control elements are typically active in a specific cell or tissue (e.g., brain, neurons). Expression control elements also can confer expression in a manner that is regulatable, that is, a signal or stimuli increases or decreases expression of the operably linked nucleic acid. A regulatable element that increases expression of the operably linked nucleic acid in response to a signal or stimuli is also referred to as an "inducible element" (i.e., is induced by a signal). A regulatable element that decreases expression of the operably linked nucleic acid in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

Expression control elements also include native elements(s). A native control element (e.g., promoter) may be used when it is desired that expression of the nucleic acid may mimic the native expression. A native element may be used when expression of the nucleic acid is to be regulated temporally or developmentally, or in a tissue-specific manner, or in response to specific transcriptional stimuli. Other native expression control elements, such as introns, polyadenylation sites or Kozak consensus sequences may also be used.

Any suitable non-viral delivery methods involving non-viral vectors can also be used. Non-viral mediated delivery of shRNA or siRNA for ΔFosB can be achieved, for example, through binding of siRNA or shRNA to natural or synthetic polymers such as, for example, PEI, poly-1-lysin and dendrimers. These polymers protect the siRNA from nuclease attack and enhance the update of siRNA to the system. Additionally, any suitable nanoparticles can be used. Examples of nanoparticles include inorganic nanoparticles, cationic lipids, cationic polymer nanoparticles, lipid-based nanoparticles, PEG-chitosan nanoparticles, PEG-oligo-chitosan nanoparticles, gold nanoparticles, gold nanoparticle conjugates, dendrimers, liposomes, magnetic nanoparticles, etc. Use of nanoparticles for delivery of nucleic acids, including siRNA, is well known and described in, e.g., Herranz et al., Microsc. Res. Tech. 2011 74(7):577-591; Giulio et al., Drug Delivery, 11:169-183, 2004; Cullis P R and H Hope M J Mol Ther. 2017 25(7):1467-1475; Zhou et al., Adv Drug Deliv Rev. 2017 (115):115-154; Liang et al., Hum Gene Ther. 2018 29(11):1227-1234; U.S. Patent Application Pub. No. 2019/0321295; and U.S. Pat. Nos. 8,871,509 and 9,764,012, all incorporated herein by reference. Examples of chemical-based non-viral vectors for gene therapy are described in Cationic Lipids, Cationic Polymers and Inorganic Nanoparticles (Al-Dosari M S, Gao X. Non-viral gene delivery: principle, limitations, and recent progress. AAPS J. 2009; 11(4):671-681, also incorporated herein by reference.

Methods for Reducing ΔFosB Expression and Activity and Treating LID in a Subject Described herein are methods for reducing ΔFosB expression or activity in a cell and treating dyskinesia (LID). These methods include contacting (e.g., transducing, transfecting, infecting) a cell with a vector (e.g., rAAV vector, recombinant lentiviral vector, non-viral vector), virus (e.g., rAAV, recombinant lentivirus), or composition as described herein. Typically, the compositions, vectors, and viruses are delivered to appropriate target cells in the subject (e.g., human patient). A typical target cell is any cell that has elevated (upregulated) levels of ΔFosB, e.g., striatal region of the brain in a person with movement disorder.

The methods include administration of any of the compositions, vectors and viruses described herein. Administration of a composition, vector or virus as described herein to the subject results in amelioration, or treatment of LID (e.g., alleviation or mitigation or elimination of LID symptoms or pathology) in a subject. In a typical embodiment, administration of a composition, virus or vector to a subject having LID reduces ΔFosB expression, and decreases or eliminates AIMS in the subject.

Combination therapies may be used to treat LID in a subject. In some embodiments, a combination therapy involves administering a nucleic acid sequence encoding shRNA specific for ΔFosB and a known or to be developed anti-LID therapeutic, e.g., amantadine. In one example of such an embodiment, a rAAV vector including a heterologous polynucleotide sequence including a nucleic acid sequence encoding a shRNA specific for ΔFosB is administered to the subject and amantadine is orally administered to the subject. In such an embodiment, the two therapeutics can be administered in the same composition simultaneously, or they can be administered at different time points (e.g., two different compositions administered at two different time points). In any combination therapy, the two or more therapeutics can be administered simultaneously, concurrently or sequentially, e.g., at two or more different time points. In one embodiment of combination therapy, a composition that reduces ΔFosB expression and a known or to be developed anti-LID therapeutic (e.g., amantadine) are admixed in the same injection or infusion volume.

Any suitable methods of administering a composition, virus or vector as described herein to a subject (e.g., a human suffering from LID) may be used. In these methods, the compositions, viruses and vectors can be administered to a subject by any suitable route, e.g., intracerebral injection or infusion. In some embodiments, recombinant virus (e.g., rAAV, recombinant lentivirus) including a nucleic acid sequence encoding shRNA specific for ΔFosB are administered to a subject via a bolus injection or infusion into the ventricles. As indicated above, the compositions described herein may be in a form suitable for sterile injection. To prepare such a composition, the suitable active therapeutic(s) (e.g., a shRNA specific for ΔFosB, a vector encoding same, a recombinant virus) are dissolved or suspended in an acceptable liquid vehicle. The compositions, non-viral vectors, viruses and viral vectors described herein may be administered to mammals (e.g., rodents, humans, nonhuman primates, canines, felines, ovines, bovines) in any suitable formulation according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999), a standard text in this field, and in USP/NF). A description of exemplary pharmaceutically acceptable carriers and diluents, as well as pharmaceutical formulations, can be found in Remington: supra. As used herein the terms "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle to a subject.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Viral vectors (e.g., rAAV vectors, recombinant lentivirus vectors), viruses, non-viral vectors, and pharmaceutical compositions thereof, can be packaged in single or multiple unit dosage form for ease of administration and uniformity of dosage.

Effective Doses

The compositions, viruses and vectors described herein are preferably administered to a mammal (e.g., human) in an effective amount, that is, an amount capable of producing a desirable result in a treated mammal (e.g., reducing ΔFosB expression, decreasing or eliminating AIMs). Such a therapeutically effective amount can be determined according to standard methods. Toxicity and therapeutic efficacy of the compositions and vectors utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. A delivery dose of a composition, virus or vector as described herein is determined based on preclinical efficacy and safety. In one embodiment of a dose for a human, the titer of AAV-sh[ΔFosB] is $1.16 \times 10^{13}$ VG/mL. Volume can range between 10 microliter and 500 microliter on each side of the mammalian (e.g., human) brain.

Kits

Described herein are kits for inhibiting ΔFosB expression or activity, and treating dyskinesia in a subject (e.g., a human having PD and LID). A typical kit includes a composition including a pharmaceutically acceptable carrier (e.g., a physiological buffer) and a therapeutically effective amount of shRNA specific for ΔFosB; and instructions for use. Kits also typically include a container and packaging. Instructional materials for preparation and use of the compositions and vectors described herein are generally included. While the instructional materials typically include written or printed materials, they are not limited to such. Any medium capable of storing such instructions and communicating them to an end user is encompassed by the kits herein. Such media include, but are not limited to electronic storage media, optical media, and the like. Such media may include addresses to internet sites that provide such instructional materials.

EXAMPLES

The present invention is further illustrated by the following specific examples. The examples are provided for illustration only and should not be construed as limiting the scope of the invention in any way.

Example 1

Role of Striatal ΔFosB in L-Dopa-Induced Dyskinesias of Parkinsonian Nonhuman Primates Long-term DA replacement therapy in PD leads to the development of LID. The transcription factor ΔFosB that is highly upregulated in the striatum following chronic L-Dopa exposure may participate in the mechanisms of altered neuronal responses to DA generating LID. To identify intrinsic effects of elevated ΔFosB on L-Dopa responses, transgenic ΔFosB overexpression was induced in the striatum of parkinsonian non-human primates kept naïve of L-Dopa treatment. Elevated ΔFosB levels led to consistent appearance of LID since the initial acute L-Dopa tests. In line with this motor response, striatal projection neurons (SPNs) responded to DA with changes in firing frequency that reversed at the peak of the motor response, and these unstable SPN activity changes in response to DA are typically associated with the emergence of LID. Transgenic ΔFosB overexpression also induced upregulation of other molecular markers of LID. These results support an autonomous role of striatal ΔFosB in the adaptive mechanisms altering motor responses to chronic DA replacement in PD and suggest that ΔFosB elevation is responsible for LID generation and that repressing its expression can have therapeutic value.

Results

Figure 1A:
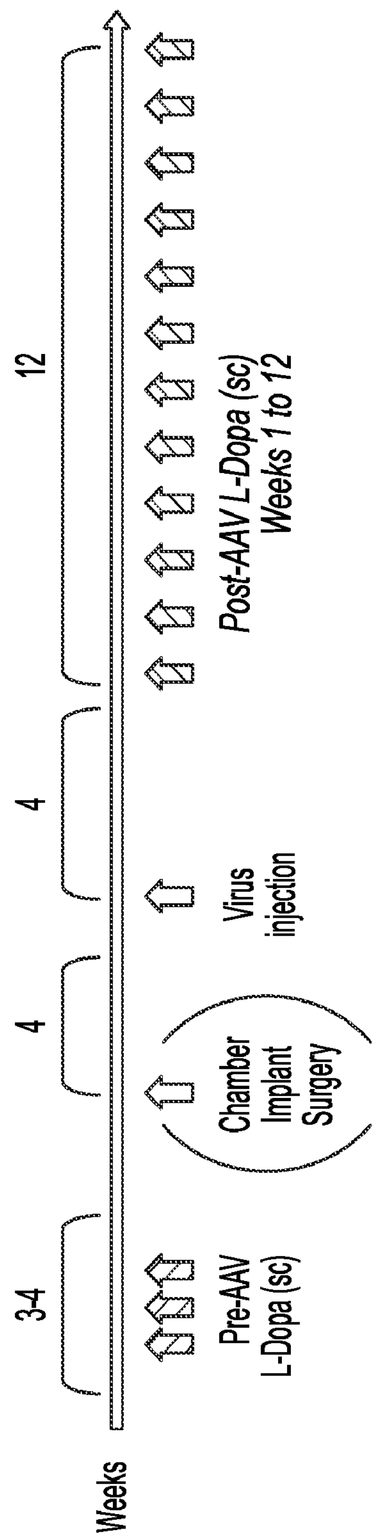
FIG. 1A shows the timeline and design of experiments described in Example 1 (overexpressing ΔFosB in primate model of PD). Timeline. Studies began for all MPTP-treated primates with assessment of the response to s.c. L-Dopa injections (blue arrows) during 3-4 weeks in order to determine effective "on" response of the selected dose, and the absence of LID in acute tests. At week 4, recording chambers were implanted surgically (only in a subgroup of 4 animals used for physiology), and four weeks later viral vectors (rAAV-ΔFosB or rAAV-eGFP) infused into the striatum accessed through the chambers. In the remaining 5 animals, viral vectors were infused under stereotaxic surgery. In all animals, 4 weeks after virus infusion, weekly acute L-Dopa tests began and continued until the twelfth week (red arrows).
Figure 1B:
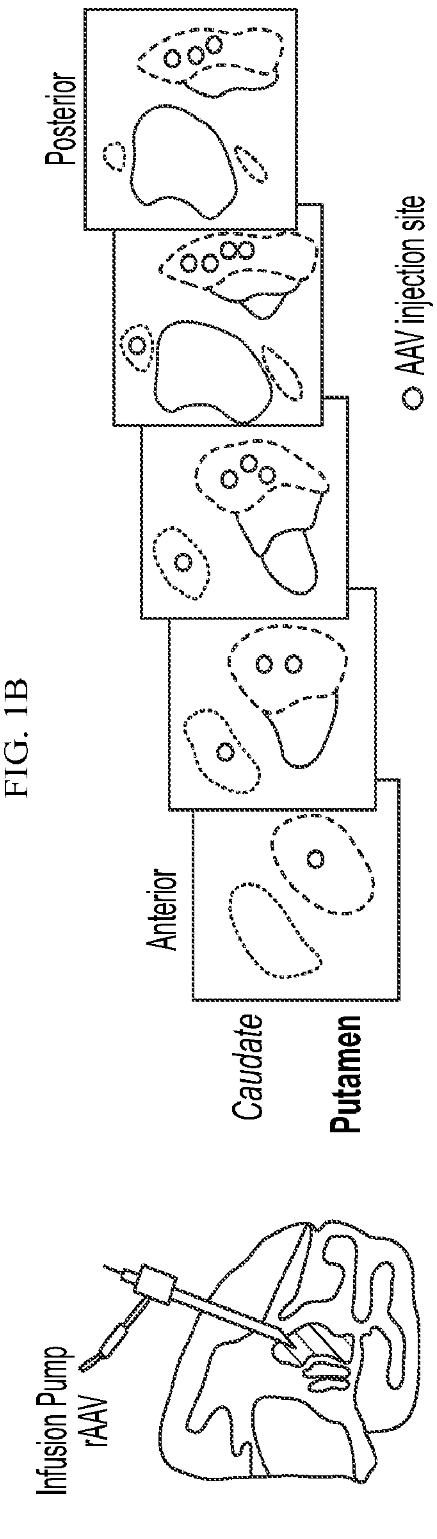
FIG. 1B is a schematic drawing of the virus injection sites illustrating the injectrode locations in the putamen, and the caudate and putamen planes from anterior to posterior regions.

Transgenic ΔFosB Overexpression in the Striatum Generates Dyskinetic Responses to L-Dopa in Parkinsonian Primates To determine the behavioral effects of transgenic ΔFosB overexpression, nine primates with stable parkinsonism (see Methods for description of the animal model developed after a series of systemic MPTP (1-methyl-4-phenyl-1,2,3,6-tetrahydropyridine) injections) and naïve of chronic dopaminergic drug exposure received bilateral striatal injections of rAAV-ΔFosB (n=5) or rAAV-eGFP (n=4) as control virus. During the month prior to virus injection, three tests of subcutaneous (s.c.) L-Dopa injections at intervals of seven days provided the baseline (pre virus) response confirming the lack of LID in the absence of chronic L-Dopa treatment in all animals. In two animals of each virus group, vectors were injected into the striatum through surgically implanted recording chambers after electrophysiologic mapping (animals prepared to analyze effects on neuronal activity). In the remaining animals, vectors were injected surgically with stereotaxic guidance. Beginning at 4 weeks post viral vector injections, the response to the predetermined s.c. L-Dopa dose was tested at weekly intervals for a total of 3 months (see timeline and location of virus injections in FIG. 1). Striatal rAAV-ΔFosB injection induced LID from the first L-Dopa test post virus injection, and LID progressed in successive weeks reaching maximal scores between weeks 6 and 8 followed by a slight decline between weeks 9 and 12. LID was not expressed in the control group injected with rAAV-eGFP during the entire assessment period of 12 weeks with the exception of one animal that began to develop LID by the ninth week. rAAV-ΔFosB-induced LID was mild to moderate choreodystonic movements variably expressed in the face, neck, and limbs with the usual predominance in lower limbs, all features indistinguishable from typical LID in the primate model. The time course of L-Dopa response shows a single peak of dyskinesias reaching the highest scores between 50 and 90 min post s.c. injection, which parallels the monophasic peak-dose LID also commonly seen in the primate. Striatal rAAV-ΔFosB injection did not induce dyskinesias without L-Dopa administration, and no animal in either rAAV group showed additional motor abnormalities or other adverse reactions post virus injection. Results in control animals exposed to the same schedule of discrete (weekly) L-Dopa tests pre and post rAAV-eGFP virus injection showing mild dyskinesias starting by week 9 indicate that LID development requires a higher level of exposure, as typically occurs with chronic daily L-Dopa treatment. In contrast, the rapid LID development in animals naïve of chronic L-Dopa exposure but injected with rAAV-ΔFosB indicates a primary role of striatal ΔFosB in LID mechanisms.

Striatal rAAV-ΔFosB injection did not induce changes in the parkinsonian "off" state (basal motor disability scores, MDS), which remained the same throughout the 12-week assessment period. More importantly, striatal rAAV-ΔFosB injection had no impact on the antiparkinsonian action of L-Dopa measured by MDS in the "on" state (reversal of parkinsonian motor disability), which remained unchanged from pre to post virus L-Dopa responses, and were not different between the two animal groups. Thus, striatal rAAV-ΔFosB injection did not lead to overall sensitization to DA with augmented L-Dopa responses that could accelerate LID development but had a specific impact on the molecular events leading to LID.

Striatal ΔFosB Overexpression Induces the Pathological Responses of Striatal Projection Neurons to DA that are Associated with Dyskinesias To determine the effect of ΔFosB overexpression on SPN responses to DA, striatal recordings performed once weekly post-virus injections were analyzed. In the control rAAV-eGFP group, the "on" state was characterized by a large predominance of stable firing changes in SPNs with either a D1-like response (increases in 75% units) or D2-like response (decreases in 88% units) during the first month of recordings (see Methods for definition of stable and unstable responses). Increasing L-Dopa exposure with weekly injections led to reduction of the stable responses and increase of unstable responses in the second and third months, ending in a similar percentage of SPNs with stable and unstable responses by the ninth week when dyskinesias began to express in this group, i.e. 50% unstable D1-like responses and 43% unstable D2-like responses.

Notably, in the rAAV-ΔFosB group, unstable responses largely predominated from the first month of recordings post virus injections. The proportion of SPNs with unstable responses was significantly higher in most recordings from the first to the twelfth week. In the first month, such pathological instability of DA responses developed in 77% of the total SPNs with D1-like response, and 75% of the total SPNs with D2-like response. Usually, unstable responses develop in ~50% of units in each SPN subset (D1- or D2-like response) following chronic daily L-Dopa treatment. The effects of ΔFosB overexpression observed in SPNs with either D1- or D2-like responses were maintained throughout the three months of the testing period oscillating between 50% and 75% unstable firing changes. Taken together, these data show the correlative development of LID and unstable SPN responses to DA with over 50% SPNs in both subsets exhibiting unstable responses to DA, but with different timing, i.e. early in the rAAV-ΔFosB group and late in the control rAAV-eGFP group. This physiological correlate indicates engagement of ΔFosB in the molecular pathways controlling responses to DA extensively across SPNs, and thereby generating dyskinesias. Analysis of pools of neurons in the "off" state showed similar SPN firing frequencies in the two viral vector groups, and no significant differences in successive weeks, indicating no effect of the transgenes (ΔFosB or eGFP) on basal SPN activity.

Increased FosB Immunopositive Neurons and ΔFosB Proteins in the Striatum Confirms Transgenic Overexpression High FosB expression was detected in striatal neurons of animals injected with rAAV-ΔFosB in comparison with control animals injected with rAAV-eGFP. The antibody used for immunostaining reacts with the N-terminus of FosB/ΔFosB, and since the virus plasmid was constructed with ΔFosB cDNA, the protein highly expressed in the rAAV-ΔFosB group is presumed to be largely ΔFosB. Therefore, the robust staining of FosB proteins in the rAAV-ΔFosB group was produced by the specific transgene expression. Double staining with antibodies against FosB and the neuronal marker NeuN showed that 86% of FosB immunopositive cells co-stained for NeuN. These findings indicate that a large majority of recorded neurons likely expressed the transgene. Cell counting in both virus groups showed a large difference in FosB expression, and the efficiency of rAAV-eGFP infection in control animals was also confirmed by eGFP immunostaining.

Increased ΔFosB expression was confirmed by Western blotting as well. While some variability was seen in the degree of overexpression among animals injected with rAAV-ΔFosB, a clear difference with an eight-fold increase in mean ΔFosB protein content was detected in comparison with the control rAAV-eGFP injected group.

Impact of ΔFosB Overexpression on Molecular Markers of LID

Comparison of striatal tissue samples between animals injected with rAAV-ΔFosB versus rAAV-eGFP showed significant differences in additional molecular markers associated with LID. Phosphorylation of DARPP-32 at Thr34, which is augmented in LID, doubled in the rAAV-ΔFosB group compared with the control group. No significant difference was detected in total DARPP-32 level. Similarly, the expression of cyclin-dependent kinase 5 (Cdk5), another protein increased in LID, was more than double in the ΔFosB group compared with the rAAV-eGFP group Similar to ΔFosB, the levels of these markers also correlated with the severity of LID. Another kinase, ERK, which is activated during priming rather than maintenance of dyskinesia, was not different between the two groups. These molecular changes suggest that elevated striatal levels of ΔFosB in parkinsonian primates can mimic the molecular microenvironment of LID.

The molecular changes detected in striatal lysates following transgenic overexpression of ΔFosB reflect some of the alterations seen in the context of chronic L-Dopa exposure. Increased phosphorylation and activation of the key regulator of striatal neuronal signaling DARPP-32 at Thr34 as well as upregulation of Cdk5 were present in this gene delivery model. These molecular analyses in transgenic ΔFosB versus control animals suggest that overexpression of the transcription factor induces upstream gene regulation likely involving key kinases and phosphatases, which can mediate the increase in p-DARPP-32. Cdk5 is a direct target of the transcriptional activity of ΔFosB. Changes in both these markers are typically present in models of dyskinesia induced by chronic L-Dopa treatment in both primate and rat models, and can be reversed by anti-dyskinetic drugs. Additionally, p-ERK, which is activated primarily following acute L-Dopa administration in rodent models of LID and diminishes with chronic L-Dopa therapy in parkinsonian primates, is not altered with sustained ΔFosB overexpression. These findings collectively support that ΔFosB overexpression per se can lead to the molecular and physiological changes forming the LID substrate. In contrast, such an autonomous role cannot be attributed to other molecular markers of LID that are also regulated by chronic exposure to L-Dopa, but remain to be examined further.

Methods

Animal Preparation

Nine adult cynomolgus macaques (*Macaca fascicularis;* 6-8 kg of weight) of both genders were used in this study in accordance with the *National Institute of Health Guide for the Care and Use of Laboratory Animals*. All animals were rendered parkinsonian by systemic weekly administration of 1-methyl-4-phenyl-1,2,3,6-tetrahydropyridine (MPTP, 0.2-0.4 mg/kg i.v.) until meeting the criteria for moderate parkinsonism (usually in 1-3 months) according to motor disability score (MDS), as measured with the standardized Motor Disability Scale for MPTP-treated non-human primates. MPTP treatment ended if MDS stabilized for a period of at least four weeks. MDS indicative of moderate parkinsonism was targeted in order to maintain animals without L-Dopa or other antiparkinsonian treatments. After stabilization, animals were evaluated for their baseline motor response to L-Dopa up to a maximum of 3 tests (one s.c. injection per week) if necessary for a clear response with consistent scores. L-Dopa methyl ester plus benserazide (Sigma Aldrich, St. Louis, MO) was used for s.c. injections. Due to the limited number of baseline tests included in the protocol, the L-Dopa dose for each animal was adjusted based on the scores in the 3 baseline tests so that in the "on" state (reversal of parkinsonism) there was a 50% reduction of MDS in all animals. These tests demonstrated the absence of dyskinesias prior to AAV injections in all animals.

Production of Recombinant AAV2/5 Viral Vectors.

In brief, pAAV-ΔFosB and pAAV-eGFP vectors were constructed as follows: the mouse ΔFosB cDNA or eGFP cDNA was cloned into pAAV-MCS plasmid (Stratagene, San Diego, CA) to generate pAAV-ΔFosB or pAAV-eGFP, respectively. To generate AAV2/5 viral particles, HEK293T cells were co-transfected with pAAV-ΔFosB, or pAAV-eGFP along with pAAV-Helper and pAAV-RC5 (VPK-425: Cell Biolabs, Inc., San Diego, CA) using a standard calcium phosphate method, and 72 h after transfection the cells were harvested. The crude recombinant adeno-associated virus (rAAV) supernatants were obtained by repeated freeze/thaw cycles and centrifugation at 10,000 g for 10 min. Effective rAAV2/5-ΔFosB expression in HEK293T cells was detected by Western blotting with primary antibody against FosB/ΔFosB (sc-7203: Santa Cruz Biotechnology, Dallas, TX). High-titer rAAV2/5-ΔFosB ($2.8\times10^{13}$ GC/ml) was prepared by Vector BioLabs (Philadelphia, PA). The number of genome copies was determined by quantitative PCR within the cytomegalovirus promoter region of the vector using primers 5'-GACGTCAATAATGACGTATG-3' (SEQ ID NO: 19) and 5'-GGTAATAGCGATGACTAATACG-3' (SEQ ID NO: 20). The generated viral vector particles were finally prepared for injection into the monkey brain at a dilution of $1\times10^{12}$ GC per

Overexpression of ΔFosB In Primates rAAV-ΔFosB and rAAV-eGFP vectors were constructed as described before (Cao et al. 2010 J Neurosci 30(21):7335-7343). Plasmids were constructed with a cassette containing chicken β-actin-promoter/cytomegalovirus enhancer (CAG promoter), which yields high expression in striatal cells. The virus was injected either under stereotaxic surgery (animals used only for behavioral assessment), or through the recording chamber after electrophysiologic mapping (animals used also for neural recordings). Both viruses were injected at equal particle doses ($1\times10^{12}$ GC/ml) into the striatum bilaterally. A total of 104 μl was injected in each hemisphere between the putamen (90 μl) and the caudate nucleus (14 μl), and this volume was distributed in 16 sites using 1 or 2 depths per injection track (total injection tracks: 12). The volume was estimated to cover entirely the posterolateral putamen and posterior portion of the caudate body, plus a large pre-commissural portion of both nuclei (see FIG. 1B).

rAAV-ΔFosB or rAAV-eGFP as control was injected into the striatum of parkinsonian monkeys. Animals were randomly assigned to each treatment group (ΔFosB or control virus, n=5 and n=4, respectively). Five animals received the virus injections directly following craniotomies under stereotaxic surgery (see below) and were used for behavioral assessment. Four animals (2 in each virus group) received the virus injections through the recording chambers that were surgically implanted in preparation for neural recordings along with the behavioral assessment. All surgeries were performed under general anesthesia and followed stereotaxic coordinates for direct virus injections or for implants of bilateral recording chambers according to previously reported procedures. The protocol for virus delivery included multiple injections covering an extended area of the primate striatum (mostly the putamen) that resulted in on-target injections in all animals following either procedure. In the 5 animals injected with virus following stereotaxic guidance under surgery, coordinates were taken from the stereotaxic atlas targeting most central areas of the sensorimotor putamen to reduce the margin of error, which is already small for a large striatal region as the putamen. In the 4 animals with recording chambers, electrophysiologic mapping of the basal ganglia was used to direct the injections into the striatum. Virus injections were performed using Hamilton syringes in microinfusion pumps (injection rate of 1 μL/min) mounted on the stereotaxic frame in surgery, or connected to an injectrode system (Alpha Omega, Alpharetta, GA) in the micromanipulator for injection through the recording chamber. rAAV-ΔFosB or rAAV-eGFP were injected at equal particle doses ($1\times10^{12}$ vg/ml) into the striatum bilaterally. A total of 104 μl was injected in each hemisphere, and the volume was distributed in 16 sites using 1 or 2 depths of injection in each site into the putamen (90 μl) and the caudate (14 μl). Target areas were the posterolateral putamen and the posterior portion of the caudate body. All animals remained free of antiparkinsonian treatment during the 4-week period post virus injection and before initiation of testing.

Behavioral Assessment

L-Dopa responses were assessed at baseline and post virus injection using the standardized Motor Disability Scale for MPTP-treated non-human primates, Part I-MDS and Part II-LID. The L-Dopa dose for each animal was pre-determined before AAV injection during baseline assessments (FIG. 1A), and the individual dose (14-21 mg/kg, s.c.) remained unchanged in all 12 post-virus assessments. In recording experiments, animals were scored while freely moving in the cage at the end of the recording. All tests were videotaped for blinded scoring.

Following the 4-week period post virus injection, behavioral tests began to assess the time course of development of LID. L-Dopa responses were tested only once weekly to avoid the chronic daily exposure that leads rapidly to LID appearance in this model. In these weekly tests, L-Dopa was given at the predetermined dose (s.c.) and the animal's motor behavior was assessed for the whole duration of the response until returning to the "off" state (baseline parkinsonian disability) score. Scores were taken before L-Dopa injection ("off" state) and thereafter every 20 min interval during the "on" state. Weekly responses were tested for a period of 12 weeks. Similarly, in the 4 animals prepared for electrophysiology, motor scores were obtained in the "off" state, and at the same intervals post-L-Dopa injection after rapid transfer to the cage at the end of collecting neural data (i.e. by the second interval of the "on" state). As the first interval after L-Dopa injection (30 min) was scored in the primate chair, scores of this interval were used for behavioral-SPN activity correlation, but they were not computed in the behavioral analysis of all animals together. Experiments were conducted in the morning when animals display the highest MDS. All behavioral tests were performed in the same testing cage, and animals were also videotaped for deferred scoring by a second blind investigator. Animals were euthanized at the end of the $12^{th}$ week of testing for analysis of ΔFosB expression and other LID markers in the striatum.

Electrophysiology

Two animals from each group (rAAV-ΔFosB and rAAV-eGFP) were used for single cell recordings every week at the same time as the behavioral assessments of weekly L-Dopa responses to avoid additional drug exposure for collection of neural data. After behavioral assessment and recordings in the "off" state, the animal received the predetermined s.c. L-Dopa dose, and the recording of neuronal activity continued during the transition to L-Dopa-induced motor states, collecting data at the onset of the "on" state, and at the time corresponding to LID peak, whether or not dyskinesias were observed. As animals were not exposed to regular daily L-Dopa treatment, LID was generally not present in the rAAV-eGFP group. In the absence of LID, data were stored at the equivalent time frame of LID in the other group. Subsequently, the animal was rapidly transferred to the cage for complete behavioral assessment during the "on" state as proceeded in the other animals. Single cell recordings in the striatum were performed using tungsten microelectrodes and standard techniques for isolation and continuous recording of SPNs. The final classification of units was always performed with offline analysis. During "off" state, 624 SPNs were analyzed from week 1 to 12.

As reported previously in continuous recordings of individual neurons during the transition to motor states, the SPN activity in the "on" state increased or decreased showing a D1- or D2-like response to DA, respectively. A total of 98 (rAAV-eGFP group) and 83 (rAAV-ΔFosB group) SPNs were recorded continuously from "off" to "on" and to dyskinesia states throughout the 12 weeks of recordings post virus injection. D2-like responses slightly predominated in both virus groups (54 out of 98 in eGFP group, and 48 out of 83 in ΔFosB group) likely due to better isolation of units with higher level of hyperactivity. Nevertheless, a considerable number of SPNs with D1-like response was recorded in each virus group (44 and 35 in eGFP and ΔFosB group, respectively). In dyskinetic animals, the increase or decrease in SPN activity developed initially in the "on" state usually reverses at the peak of the motor response in a large number of neurons, typically 50% and above. This reversal of the SPN activity changes by a significant difference ($p<0.01$ in each neuron) during the "on" state, which is called "unstable" response reveals the inability to sustain the response to DA modulation. Such widespread pathological instability of SPN responses is distinctively associated with the expression of dyskinesias. By contrast, a "stable" response to DA is characterized by an increase or decrease in SPN firing frequency that does not significantly change during the peak-dose effect.

The animal was transferred to the recording suite in a primate chair for head restraining, and motor behavior was continuously monitored through videotaping Similar to the virus injections, references for recordings in the sensorimotor putamen (posterolateral area) were provided by the preceding basal ganglia mapping. Standard techniques were used for striatal recordings. The activity of single cells was recorded with tungsten microelectrodes (FHC Inc, Bowdoin, ME; customized microelectrodes original impedance 2-4 MΩ at 1 kHz, reconditioned to 0.1-0.3 MΩ to improve the isolation of SPNs). Electrodes were lowered to the target area through an electronically controlled microdrive (NAN Instruments Ltd, Nazaret Illit, Israel). Signals were amplified and high band-pass filtered at 0.8 kHz (sampling frequency=30-40 kHz; Plexon Inc, Dallas, TX, and Blackrock Microsystems LLC, Salt Lake City, UT). Real-time sorting was used to isolate single cells and monitor their activity during testing. Typical firing patterns of tonically active cholinergic interneurons and fast-spiking GABAergic interneurons that could be recognized online by their waveform and activity pattern were excluded, and the search for units compatible with SPNs continued for data collection in the "off" state. The final classification of units was always performed with offline analysis (see below). Before proceeding with an isolated SPN to record activity changes before and after L-Dopa injection, three to four different SPNs were recorded (3 min segments) in the "off" state as a measure of changes in baseline firing frequency throughout the course of the $12^{th}$ week period. Subsequently, the last isolated SPN was monitored for several minutes before recording the baseline segment ("off" state) and proceeding with L-Dopa injection at the predetermined dose (s.c.) for the subsequent recording segments. After 3-min of data collection for the "off" state and subsequent L-Dopa injection, the isolated SPN was continuously recorded while monitoring the animal's behavior for changes indicating the transition to the "on" state (rapid movements of the eyes, increased blinking, occasional yawning, and limb stretching). The onset of the "on" state began approximately 15-20 minutes after the s.c. injection of L-Dopa. The SPN activity was collected again for 3 min corresponding to the "on" state following recognition of clear behavioral changes. The LID state usually developed 15-20 minutes after turning "on" (30-40 min after L-Dopa injection) and was indicated by the presence of typical movements unique to each animal but most commonly choreiform and dystonic movements of the legs and arms. After clear dyskinesias were observed, the SPN activity was collected again for 3 min for the dyskinesia state. However, as animals were not exposed to regular daily L-Dopa treatment, LID was generally not present in the rAAV-eGFP group. In the absence of LID, data were stored from 37-40 min after L-Dopa injection for an equivalent time period of 3 min. The stored segments were always ≥3 min. If the baseline activity was held throughout the total duration of the experiment, the offline analysis yielded 1 or 2 units per experiment.

In the "off" state, the activity of multiple SPNs was collected in every weekly session before L-Dopa injection for a total of 14 to 36 neurons per week in each rAAV-eGFP (n=2) and rAAV-ΔFosB (n=2) group. A total of 624 SPNs during "off" state were analyzed from week 1 to 12. A total of 181 SPNs were recorded continuously in complete experiments of L-Dopa injection ("off", "on" and "LID" states) from week 1 to 12.

Immunohistochemistry and Immunoblotting

Animals were euthanized following IACUC guidelines and perfused through the heart with saline solution. The brain was collected, blocked, and each hemisphere randomly assigned to fresh dissection of the striatum for immunoblotting (IB) or post-fixation for immunohistochemistry (IHC). Brain tissues from a total of 6 randomly selected animals, 3 monkeys injected with rAAV-ΔFosB and 3 monkeys injected with rAAV-eGFP, were used for IHC. Brain blocks were fixed overnight in 4% paraformaldehyde in PBS, and then immersed in PBS containing 10% and 20% sucrose for 24 h, respectively. Coronal sections (40-μm) were cut serially using a freezing microtome, and free-floating sections were washed in PBS containing 0.05% Triton X-100 (PBS-T) and then incubated for 30 min with 0.3% $H_2O_2$ to quench endogenous peroxidase activity. Sections were soaked with blocking agents and then incubated with primary antibodies dissolved in dilution reagent at 4° C. for 24 h. Normal Goat Serum Blocking Solution (S-1000, Vector Laboratories, Burlingame, CA) was used for blocking. A rabbit polyclonal antibody against FosB (1:100, sc-48, Santa Cruz Biotechnology, Dallas, TX) was used as the primary antibody. Goat biotinylated anti-rabbit immunoglobulin (BA-1000, Vector Laboratories) was used as the secondary antibody. After incubating sections for 60 min with VECTASTAIN® ABC reagent, reaction products were visualized using DAB substrate kit (PK-6100 and SK-4100, both reagents from Vector Laboratories). For double IHC, two primary antibodies were combined, including antibodies against FosB (1:100, rabbit polyclonal, Santa Cruz Biotechnology) and NeuN (1:100, mouse monoclonal, MAB 377, Millipore, Burlington, MA). Alexa Fluor® 488 goat anti-rabbit IgG (H+L) antibody (A-11008, ThermoFisher Scientific, Waltham, MA) and Alexa Fluor® 568 goat anti-mouse IgG (H+L) antibody (A-11004, ThermoFisher Scientific) were used as the secondary antibodies. Images were obtained using ECLIPSE E800 (Nikon, Tokyo, Japan). For cell counting, 10 images were obtained using a digital camera connected to a microscope (20× objective) in each animal, and FosB-positive cells were counted.

Immediately after harvesting the brains, the striatum was dissected and rapidly stored at −80° C. until processing. Striatal tissue was homogenized in 1% SDS in PBS containing phosphatase inhibitor cocktail set II (Calbiochem, La Jolla, CA) and protease inhibitor cocktail set V (Calbiochem). Lysates (50 μg) were mixed with lithium dodecyl sulfate-sample loading buffer (Life Technologies, Grand Island, NY), electrophoresed on a NuPage 4-20% (GenScript, Piscataway, NJ), and separated proteins were transferred to a polyvinylidine fluoride membrane (Bio-Rad, Hercules, CA). Membranes were blocked with 5% BSA (Sigma-Aldrich, St. Louis, MO) in Tris-buffered saline and 0.1% Tween-20 before probing with antibodies. ECL Plus (Perkin-Elmer, Waltham, MA) was used to develop immunoblots, and band intensity was quantified by ImageJ. Primary antibodies used were: FosB and pERK (Cell Signaling Technology, Danvers, MA); DARPP-32, p-T34-DARPP-32, and Cdk5 (Santa Cruz Biotechnology, Dallas, TX); and β-actin (Sigma-Aldrich, St. Louis, MO).

Statistics

Behavioral data were compared across animal groups of virus injections (rAAV-ΔFosB or rAAV-eGFP) and time. Data were processed to obtain the following parameters; 1) total dyskinesia score, 2) peak dyskinesia score, 3) itemized scores, i.e.: dyskinesia observed in neck and face (cephalic), upper limbs, or lower limbs, and 4) total MDS scores at 0 min ("off" state) and 70 min after L-Dopa injection ("on" state). These scores were calculated for each animal pre-virus injection (baseline score) and at each of the 12 weeks of testing post virus injection. All data composed continuous variables (decimal points in score values) and were analyzed with ANOVA for repeated measures and post-hoc Fisher's test if the ANOVA F value was significant.

Electrophysiology data were analyzed first with offline spike-sorting of each recording segment separately using principal component analysis (PCA; Plexon Offline Sorter). After sorting, specific waveform parameters in the clusters were applied to classify units. In addition, the established criteria for striatal unit classification was applied according to activity parameters. Units classified as TANs and FSIs or unclassified units (ambiguous parameters) were excluded from further analysis. Classified SPNs in the "off" state were followed in subsequent segments of the experiment for comparison, verifying consistency of cell isolation through all segments. The obtained sorted and classified data were then minimally post-processed using Matlab (MathWorks, Natick, MA). Spike trains for each segment (180 seconds at a minimum) were analyzed for firing frequencies binned at 1 second. Mean frequencies of pools of units recorded in the "off" state throughout the 12-week period were compared between virus groups with two-way ANOVAs. Mean frequencies of each unit in the "off", "on", and dyskinesia states were compared with one-way ANOVAs for repeated measures. Post-hoc Bonferroni's test was applied when the ANOVA F value was significant ($p<0.01$). SPNs with significantly increased or decreased firing frequency in the "on" state ($p<0.01$) were separated accordingly, i.e. increase or decrease response in the "on" state. Only three cells with no significant firing rate change in the "on" state ($p>0.05$) were excluded from further analysis. A predetermined threshold of change in the "on" state for inclusion was not used, which would be arbitrary; instead, all units with changes that were statistically significant were included. In each SPN, frequency changes in the dyskinesia state determined if the increased or decreased firing rate in the "on" state was stable or not. Unstable responses were defined by statistically significant ($p<0.01$) firing rate changes in the dyskinesia state in the opposite direction to the changes developed in the onset of the "on" state. The progression of unstable responses to L-Dopa was also analyzed over the 12-week period in each group of rAAV and then correlated with the development of LID.

Example 2

Gene Silencing of Striatal ΔFosB Reduces Abnormal Involuntary Movements Induced by L-Dopa in Hemiparkinsonian Rats Long-term dopamine replacement therapy in PD leads to the development of motor complications including LID. Previous studies have shown that the transcription factor ΔFosB plays a crucial role in the development of LID. As described in Example 1, experiments in rodent and primate models of PD demonstrated that the transgenic ΔFosB overexpression in the striatum induces rapid development of AIMs in the absence of the typically required regular L-Dopa treatment. To confirm the key role of this transcription factor, whether inhibiting ΔFosB expression reduces and/or delays AIMs development was investigated. rAAV-ΔFosB shRNA-GFP or the control virus (rAAV-scrambled shRNA-GFP) was injected into the left striatum of rats with 6-hydroxydopamine lesions of the left medial forebrain bundle. Four weeks after surgery, animals started to receive daily L-Dopa administration for 18 days. The whole L-Dopa motor response and AIMs were assessed twice a week, using standardized rating scales for rodents. AIMs scores were significantly reduced in the rats injected with rAAV-ΔFosB shRNA compared to animals injected with the control virus over the course of chronic L-Dopa treatment. Western blot analysis of striatal brain tissue showed decreased ΔFosB expression in rats injected with rAAV-ΔFosB shRNA compared to control vector injected animals. Additionally, there was a correlation between ΔFosB expression level and AIMs scores. Rotation counts, and scores from cylinder and stepping tests were no different between the two groups, indicating that gene silencing of striatal ΔFosB had no impact on the antiparkinsonian action of L-Dopa. These results confirm the crucial role of ΔFosB in the underlying mechanisms of AIMs, and suggest that ΔFosB gene silencing is a useful therapeutic approach for LID.

The development of LID is supposed to involve morphological changes as well as altered function of striatal projection neurons (SPNs) as a result of chronic DA loss and long-term replacement therapy. While the mechanisms underlying LID are not fully understood yet, several molecular markers such as ΔFosB, the phosphorylation of DARPP-32 (DA- and cAMP-regulated phosphoprotein, 32 kDa), ERK1/2 (extracellular signal related kinase), and Ser10-histone H3 have been identified for the development of LID. Especially, high expression of ΔFosB in the striatum is supposed to have a strong association with LID. ΔFosB, a truncated splice variant of FosB, is a highly stable transcription factor and its striatal expression increases after chronic drug exposure including L-Dopa. ΔFosB is also reported to increase in the striatum of human patients with PD, and moreover, previous studies have shown that a linear correlation between striatal ΔFosB levels and the severity of LID was observed in animal models of PD.

As described in Example 1, it was demonstrated that striatal overexpression of ΔFosB directly developed LID in primate models of PD without chronic L-Dopa treatment, and also induced abnormal response to DA of SPNs which is deeply associated with LID. In the present Example, it has been shown that gene suppression of striatal ΔFosB reduced AIMs induced by chronic L-Dopa treatment without impacting the action of L-Dopa in rat models of PD. These results suggest a causal relationship between ΔFosB and LID, and support a potential of gene therapy for LID in chronic PD patients with dyskinesia.

Materials and Methods

Cell Culture and Transfection

Rat PC12 cells were cultured in 12-well plates in Dulbecco's modified eagle's medium (DMEM) containing 10% fetal bovine serum (FBS) and 5% horse serum in a $CO_2$ incubator at 37° C. To test the efficiency of ΔFosB siRNAs (siRNA #1, siRNA #2 and siRNA #3—FIG. 4B), cells were transfected with siRNAs using Lipofectamine RNAiMAX (Invitrogen) according to the manufacturer's instructions for 24 hours. The medium was replaced with fresh medium containing 0.5% FBS for another 24 hours, following by induction of ΔFosB expression with 20% FBS for 2 hours. Cell lysates were then collected for Western blot analysis.

siRNA Design and Production of AAV2/5 Viral Vectors

ΔFosB lacks the C-terminal 101 amino acids of FosB as a result of alternative splicing leading to a frame shift and premature termination codon (Yen et al., 1991 PNAS 88(12):5077-5081). Thus, only the junction sequence after splicing can be used to design siRNA specific to ΔFosB (indicated as the lower box in FIG. 4A). Three siRNAs were designed based on this junction sequence and evaluated by transient transfection of PC12 cells followed by Western blot analysis (FIG. 4B). ΔFosB shRNA (based on siRNA #1 sequence) expressed from AAV2/5 viral vector was designed as follows. An oligonucleotide containing DNA sequences (SEQ ID NO: 15 and SEQ ID NO: 16) corresponding to sense and antisense strands of shRNA #1 (SEQ ID NO: 1 and SEQ ID NO: 2, respectively), with a loop (TTCAAGAGA) in between, and flanked by restriction sites was synthesized. This oligonucleotide was then cloned in a rAAV2/5 cis vector under the control of U6 promoter, with GFP co-expression under the control of CMV promoter. The cis and trans plasmids were then co-transfected into HEK293 cells to produce AAV-sh[ΔFosB]. The number of genome copies was determined by quantitative PCR. The control non-targeting vector AAV-sh[NT] was isogenic to AAV-sh[ΔFosB], except that it expressed a nontargeting shRNA (sense: AGUACUGCUUACGAUACGG (SEQ ID NO: 21)); antisense: CCGUAUCGUAAGCAGUACUU (SEQ ID NO: 22)) instead of shRNA #1. The titer of AAV-sh[ΔFosB] was $1.16\times10^{13}$ VG/mL, and the titer of AAV-sh[NT] $1.23\times10^{13}$ VG/mL.

Animals and Surgery

Figure 2:
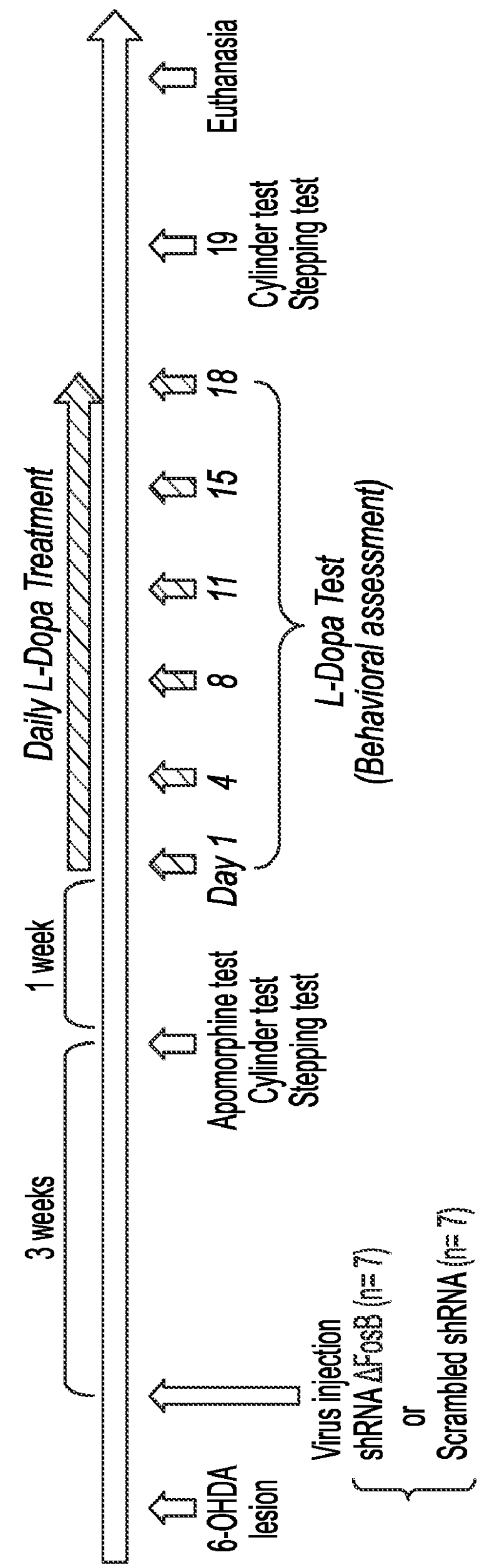
FIG. 2 illustrates the timeline and design of the experiments described in Examples 1 and 2 below. Studies began for all rats with unilateral 6-OHDA lesions of the nigrostriatal pathway, and then rats were assigned to rAAV infusion (AAV-sh[ΔFosB] or AAV-sh[NT] groups) randomly. Three weeks after these surgeries, apomorphine tests were conducted to confirm the complete lesions, and on the following day cylinder test and stepping test were performed for the baseline assessment. One week after these tests, daily i.p. injections of L-Dopa (12 mg/kg) plus benserazide (12 mg/kg) started for all rats (on day 1, blue arrow). On days 1, 4, 8, 11, 15, and 18, the whole L-Dopa motor response (rotation and AIMs) were assessed. On day 19, cylinder and stepping tests were performed again before euthanasia.

Timeline of this study is shown in FIG. 2. All procedures were approved by the Institutional Animal Care and Use Committee and were in accordance with the National Institutes of Health Guide for the Care and Use of Laboratory Animals. Male Sprague-Dawley rats (150-250 g, n=13, Charles River, Wilmington, MA) were housed with free access to food. and water, 12 h light/dark cycle, constant temperature and humidity. Rats were deeply anesthetized and injected unilaterally in the medial forebrain bundle with 6-hydroxydopamine (6-OHDA, Sigma-Aldrich, St. Louis, MO, 8 μg in 0.02% ascorbic acid in saline) under stereotaxic surgery as described previously. 6-OHDA was injected at a rate of 0.5 μl/min, and the syringe was kept in place for an additional 3 min to allow diffusion before it was slowly retracted. After 6-OHDA injection, rats were randomly assorted in two groups for virus injections into the striatum. AAV-sh[ΔFosB] (n=6) or the control virus (rAAV-scrambled shRNA-GFP, n=7) were injected at equal particle doses stereotaxically into the middle-posterior area of the striatum, on the side ipsilateral to the 6-OHDA lesion, at A: 8.4 and L: 4.4 mm from the middle of the interaural line, with two infusions at different depths, 6.2 and 5.2 mm from surface of the skull of 3 and 2 μl each. The viral vectors were injected in the middle portion of the posterior striatum to allow for diffusion within the limits of the nucleus. These injections were done with a Hamilton micro-syringe at a rate of 0.5 μl/min.

Behavioral Screening and Baseline Tests

Three weeks after surgery, rats were tested for rotational responses to a subthreshold dose of apomorphine (0.05 mg/kg, s.c. injection), and animals whose rotational behavior was >7 turns/min were selected for the study (n=13). The cylinder test and the stepping test were also performed before and after i.p. injection of L-Dopa (12 mg/kg) plus benserazide (12 mg/kg). In cylinder test which is designed to evaluate asymmetry of locomotion, animals are individually placed in a 20-cm-diameter glass cylinder, and the weight-shifting movements of the forepaws in contact with the wall of the cylinder are scored with a total of 20 contacts. The data are presented as the use of the right (impaired) paw in percentage of total touches. In the stepping test, initiation time and the number of adjusting steps were measured in each rat. In brief, each rat was held by the experimenter with one hand fixing the hindlimbs, and "initiation time" was measured until the rat initiated movement with the right forelimb not fixed by the experimenter, using 180 s as break-off point. To count the number of "adjusting steps" was counted for both paws in the backhand and forehand directions of movement, a rat was held in the same position as described above with one paw touching the table, and was then moved slowly sideways (5 s for 0.9 m) by the experimenter.

L-Dopa Treatment and Behavioral Assessment (AIMs Score)

Four weeks after virus injection, all rats started to receive daily i.p. injection of L-Dopa (12 mg/kg) plus benserazide (12 mg/kg) for eighteen days. AIMs were scored using the standardized scale described by Lee et al. (2000 Brain: A Journal of Neurology 123 (Pt 7):1365-1379). Animals were observed and scored directly by a blinded examiner every 15 min for 120 Min after L-Dopa injection. To increase the specificity of behavioral data, contraversive rotation was not included in the analysis of total AIMs. Scores in each interval were added to obtain a total value of the AIMs category for each animal in each test. Rotational behavior was measured using an automated rotometer for the whole duration of the L-Dopa response. The program counted rotations in either direction every 5 min intervals. Full circle rotations contralateral to the lesion were computed for analysis of L-Dopa responses. Peak rotation was taken from the maximum number of contralateral turns in any 5 min interval. All animals were assessed directly by a blinded examiner. On the final day (Day 19), the cylinder test and the stepping test were performed again before and after i.p. injection of L-Dopa (12 mg/kg) plus benserazide (12 mg/kg).

Tissue Preparation

All rats were deeply anesthetized and sacrificed by decapitation. Brain tissues were rapidly removed and dissected on dry ice. In all rats, posterior striatum tissues were quickly frozen on dry ice and stored at −80° C. for Western blotting. In six rats (three rats in each group), the rest of brain tissues including anterior portion of the striatum were immersed in 4% paraformaldehyde in PBS and fixed for 24 h, and then immersed in 30% sucrose in PBS until sinking. For immunohistochemistry, coronal sections of the brains were cut serially at 20-μm thickness using a cryostat (Leica Microsystems, Wetzlar, Germany).

Immunoblotting

Lysates of cultured cells and rat striatal tissue samples were extracted in 1% SDS in PBS containing phosphatase inhibitor cocktail set II (Calbiochem, La Jolla, CA) and protease inhibitor cocktail set V (Calbiochem). Three mL of buffer was used per 150 mg of striatal tissue. Samples were sonicated and cleared at 140,000×g for 10 min. Protein concentrations were determined using the BCA assay (Pierce). Lysates (20 μg) were mixed with lithium dodecyl sulfate-sample loading buffer (Life Technologies, Grand Island, NY), separated on a NuPage 4-20% (GenScript, Piscataway, NJ), and transferred onto a polyvinylidine fluoride membrane (Bio-Rad, Hercules, CA). Blots were blocked in 5% BSA (Sigma-Aldrich, St. Louis, MO) in Tris-buffered saline and 0.1% Tween-20 before probing with antibodies. ECL Plus (Perkin-Elmer, Waltham, MA) was used to develop immunoblots, and band intensity was quantified by ImageJ. Primary antibodies used were: FosB and GFP (Cell Signaling Technology, Danvers, MA); and β-actin (Sigma-Aldrich, St. Louis, MO).

Immunohistochemistry

Free-floating sections were washed in PBS containing 0.05% Triton X-100 (PBS-T) and then incubated for 30 min with 0.3% $H_2O_2$ to quench endogenous peroxidase activity. The sections were soaked with blocking agents and then incubated with primary antibodies dissolved in dilution reagent at 4° C. for 24 h. Normal Goat Serum Blocking Solution (Vector Laboratories, Burlingame, CA) was used for blocking. The primary antibodies used were mouse monoclonal antibodies against FosB (1:100, se-48, Santa Cruz Biotechnology), GFP (1:100, ab1218, Abcam), NueN (1:100, MAB377, Millipore, Burlington, MA), GFAP (1:100, sc-33673, Santa Cruz Biotechnology), and Iba-1 (1:100, sc-32725, Santa Cruz Biotechnology). Goat biotinylated anti-mouse, immunoglobulin (Vector Laboratories) was used as the secondary antibody. After incubating sections for 60 min with VECTASTAIN® ABC reagent, reaction products were visualized using DAB substrate kit (both reagents from Vector Laboratories). The sections were mounted on glass slides and counterstained with hematoxylin. For immunofluorescence, Alexa Fluor® 488 goat anti-mouse IgG (H+L) antibody (ThermoFisher Scientific, Waltham, MA) was used as the secondary antibodies. Images were obtained using ECLIPSE E800 (Nikon, Tokyo, Japan). For cell counting, 10 images were obtained using a digital camera connected to a microscope (40× objective) in each animal, and GFP-positive cells were counted.

Statistical Analysis

Measurements of behavioral effects composed parametric data that were analyzed using 1- or 2-way analysis of variance (ANOVA) for repeated measures followed by Fisher's Least Significant Difference (LSD) test when the F indicated significance. All data are presented as mean±S.E.M. Statistical significance was determined at $p<0.05$.

Results

Viral vector injection of AAV-sh[ΔFosB] or control AAV-sh[NT] in striatum had no effect on baseline motor deficits in both groups. Before starting daily L-Dopa treatment (Day 0, baseline), motor assessment was performed in all rats using cylinder test and stepping test. As shown in FIG. 6, there was no significant difference in scores obtained by cylinder test (% of the use of the impaired paw, FIG. 6A) and stepping test (initiation time [FIG. 6B] and adjusting steps counted for both paws in the backhand and forehand directions of movement [FIGS. 6C-6F]) between the two groups of rats. These results suggest intra-striatal virus infusion showed no effect on parkinsonian motor deficits in the contralateral limbs.

Figure 3A:
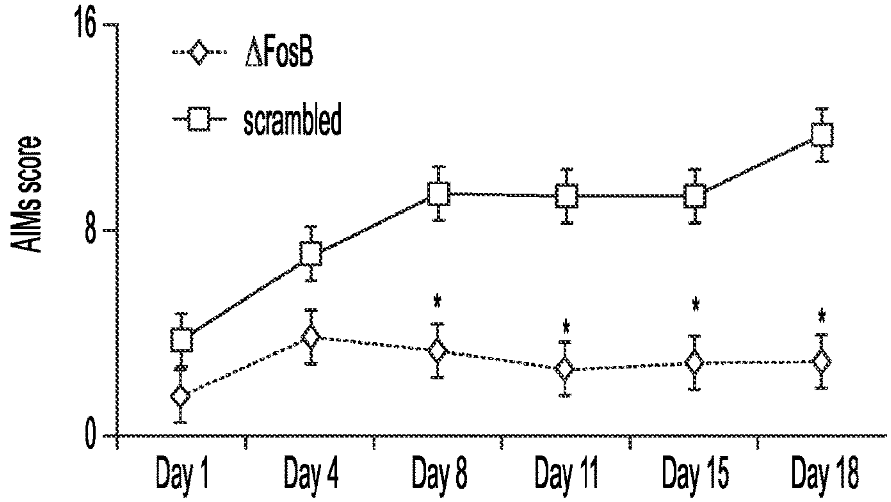
FIGS. 3A, 3B, and 3C are a series of graphs showing gene silencing of striatal ΔFosB reduced AIMs induced by chronic L-Dopa treatment in the rat 6-hydroxydopamine lesion model. AIMs score (FIG. 3A), total (FIG. 3B) and peak (FIG. 3C) rotational responses induced by i.p. injection of L-Dopa (12 mg/kg) plus benserazide (12 mg/kg) in both rat groups are presented.

Striatal ΔFosB gene silencing using AAV-sh[ΔFosB] reduced AIMs induced by L-Dopa without compromising anti-parkinsonian effect. As expected, rats that received control virus exhibited mild AIMs even in response to the first i.p. injection of L-Dopa (12 mg/kg) plus benserazide (12 mg/kg) (Day 1) four weeks after the intrastriatal viral vector infusion, and moderate to severe AIMs developed eight days after starting daily L-Dopa treatment (FIG. 3A). On the other hand, rats with striatal injection of rAAV-shRNA ΔFosB began to develop mild AIMs until Day 4, however, the development of AIMs was inhibited from Day 8 till the end of the study (Day 18) with statistical significance ($p<0.05$) in comparison with rats injected with control virus (FIG. 3A).

Figure 3B:
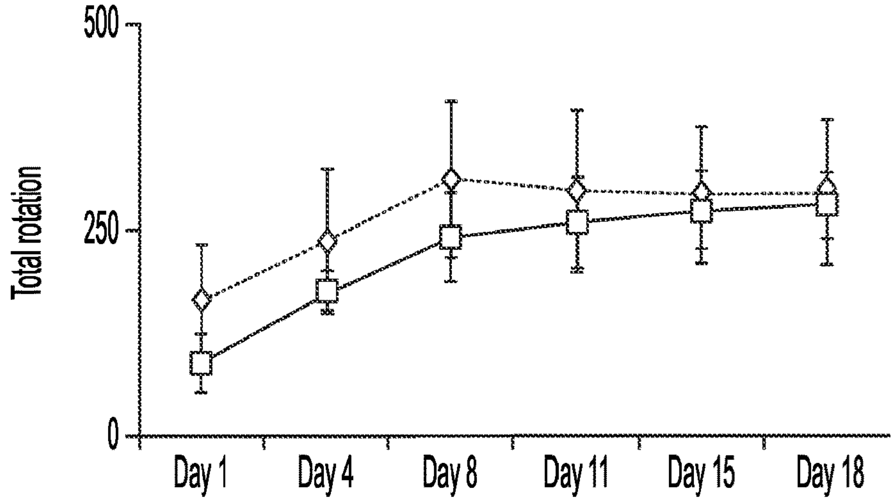
Figure 3C:
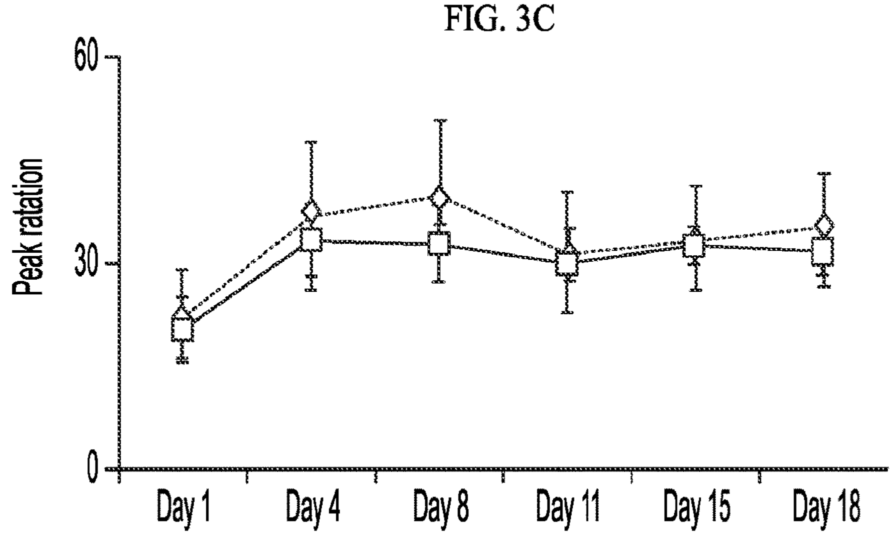
Figure 7A:
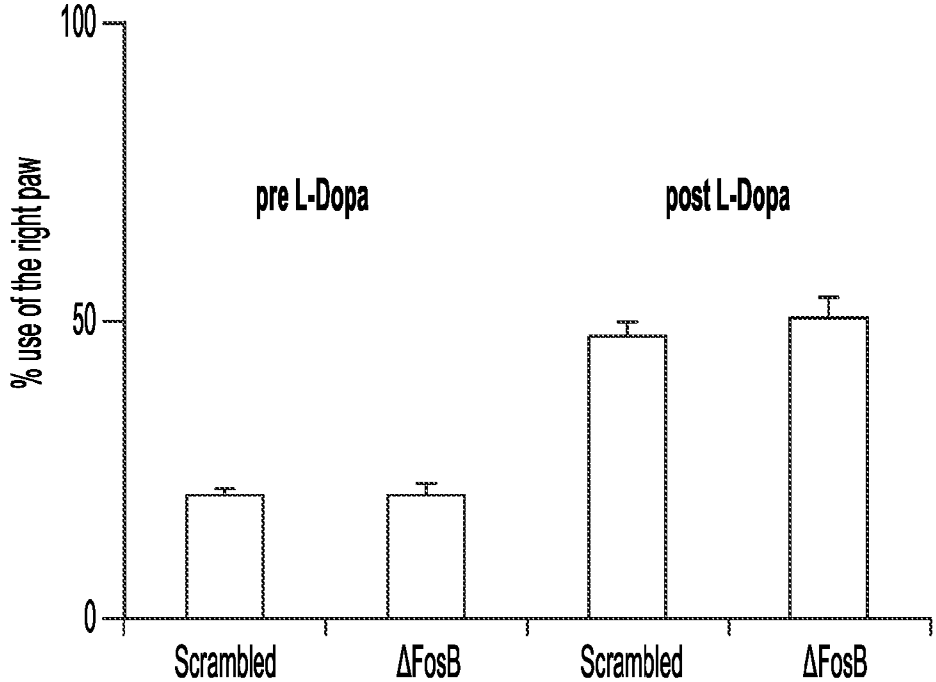
FIGS. 7A, 7B, 7C, 7D, 7E and 7F are a series of graphs showing that knockdown of ΔFosB using AAV-sh[ΔFosB] did not modify the sustained beneficial effects of L-Dopa on parkinsonian deficits following chronic therapy. Cylinder test (FIG. 7A), initiation time (FIG. 7B), and adjusting steps (FIGS. 7C-7F) performed before and after L-Dop/benserazide injection on Day 19 of a series of daily L-Dopa injections. See details of graphs in the homologous panels of FIG. 2.
Figure 7B:
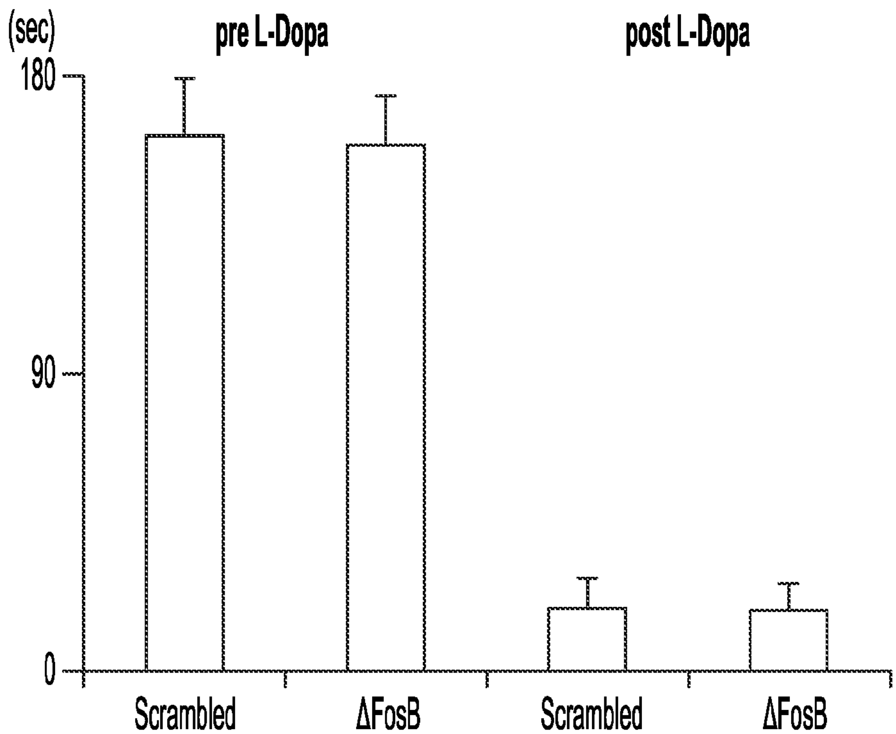
Figure 7C:
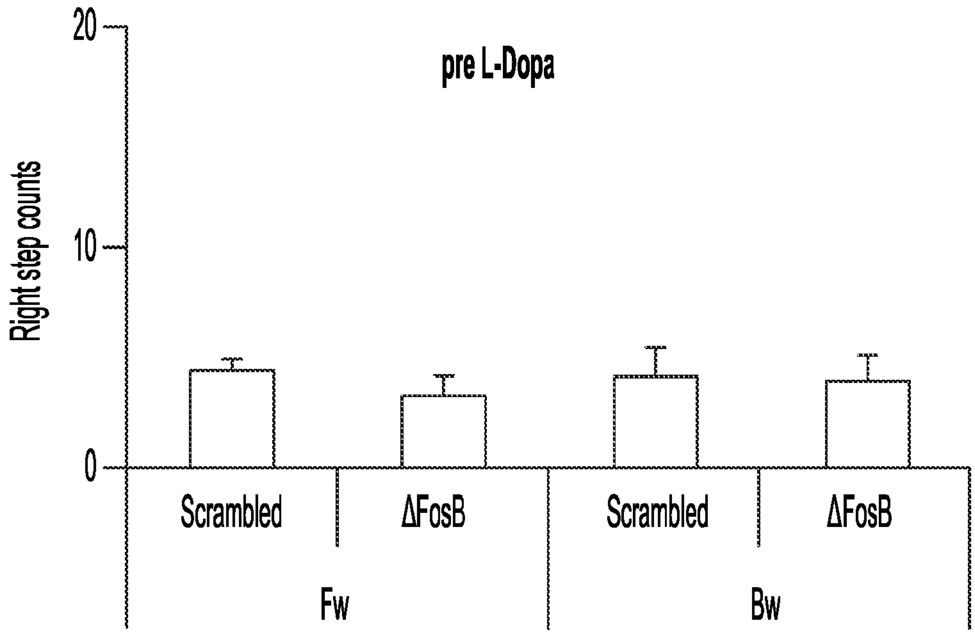
Figure 7D:
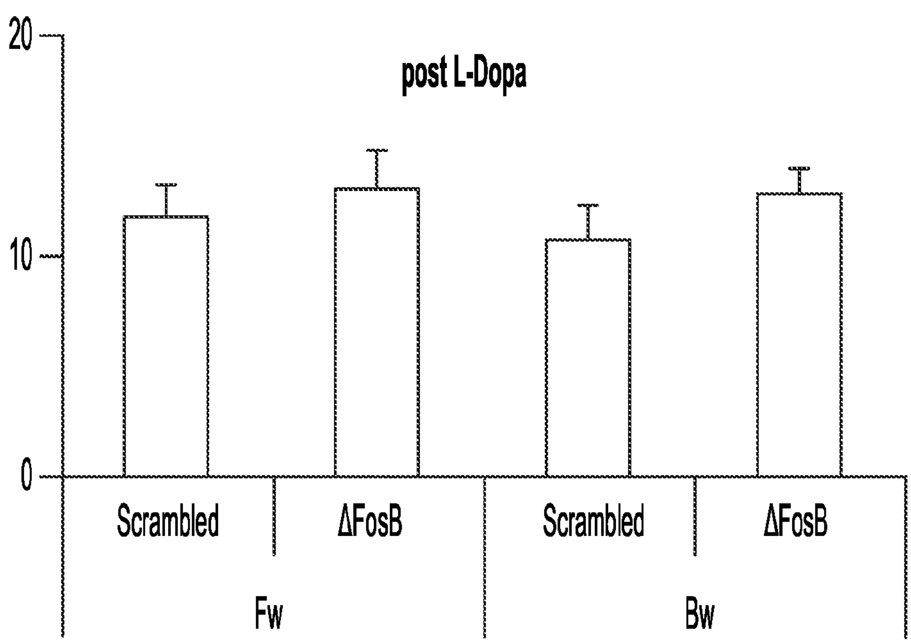
Figure 7E:
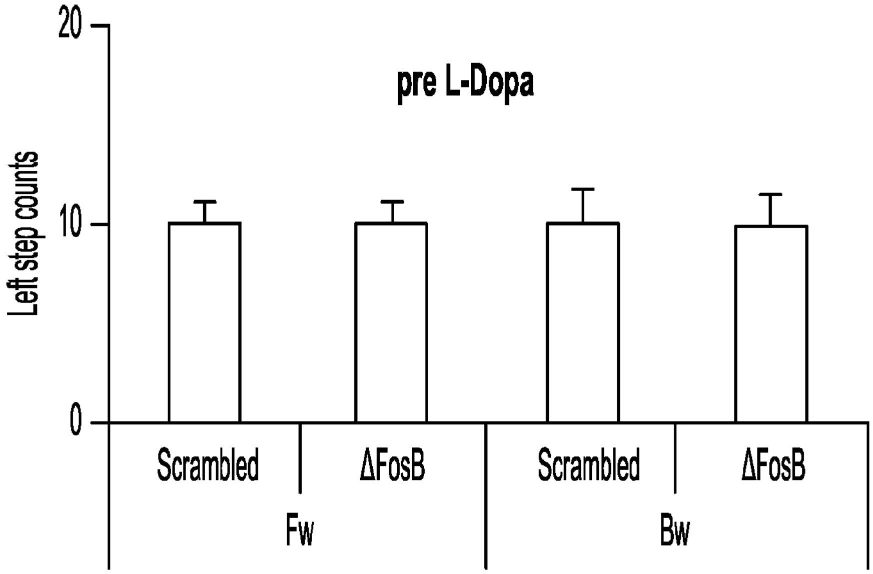
Figure 7F:
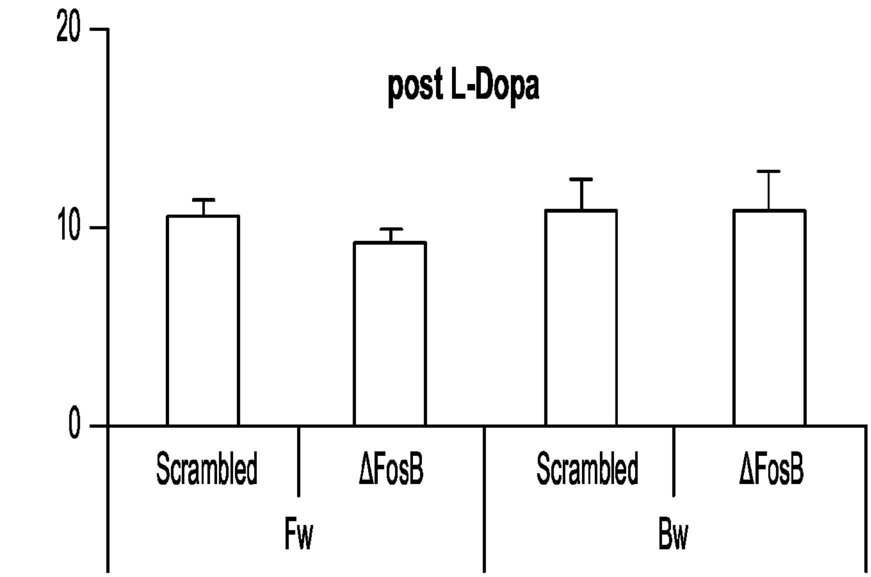

Hemi-parkinsonian rats show contralateral rotations after L-Dopa administration. In this experiment, there was no significant difference in the total and peak counts of rotation in response to i.p. injection of L-Dopa plus benserazide between rats injected with rAAV-shRNA ΔFosB and control rats from Day 1 till Day 18 (FIGS. 3B and 3C). Moreover, in scores obtained by cylinder test (FIG. 7A), initiation time (FIG. 7B), and adjusting steps counted for both paws in the backward and foreward directions of movement (FIGS. 7C-7F) on Day 19, no significant differences were observed between the two groups of rats before and after i.p. injections of L-Dopa.

Confirmation of ΔFosB Gene Silencing with AAV-sh [ΔFosB] and Impact on LID.

Figure 4D:
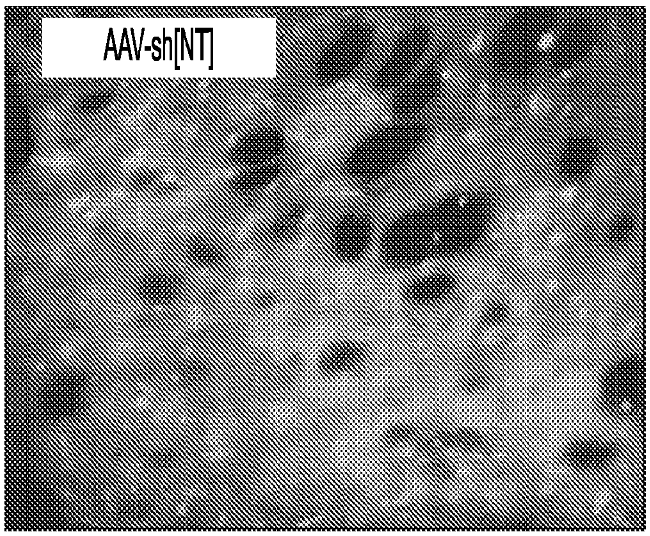
Figure 4E:
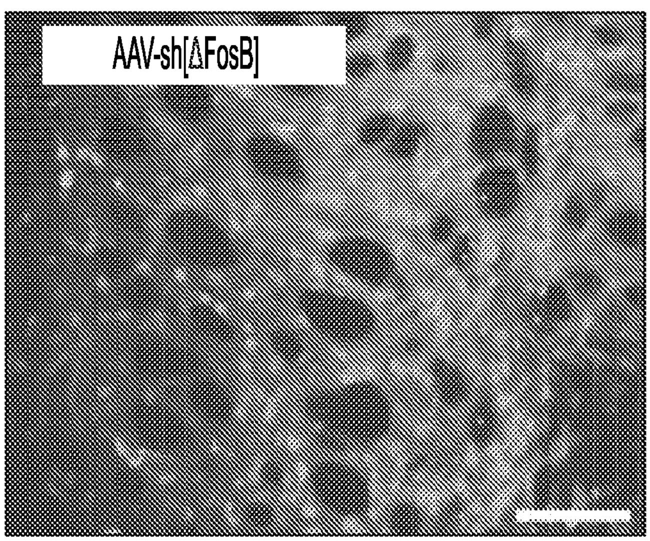
Figure 8A:
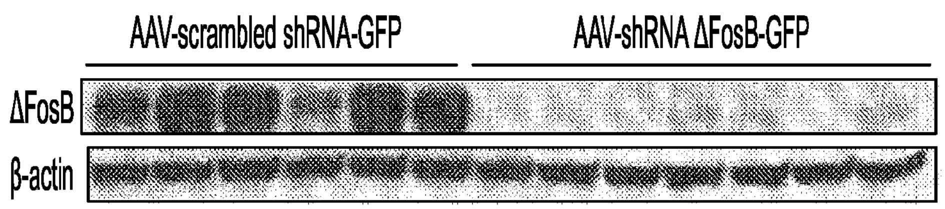
FIGS. 8A and 8B are a Western blot and a pair graphs showing confirmation of ΔFosB knock-down and correlation with severity of AIMS n the rats.
Figure 8B:
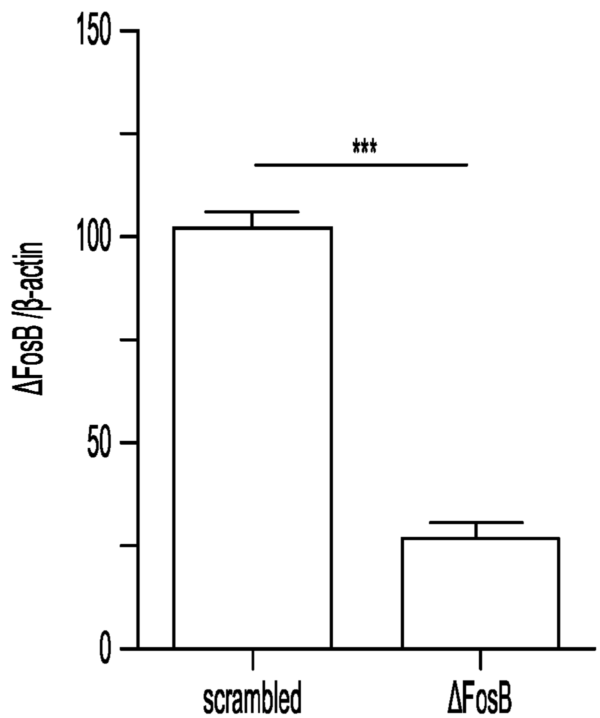
Figure 8C:
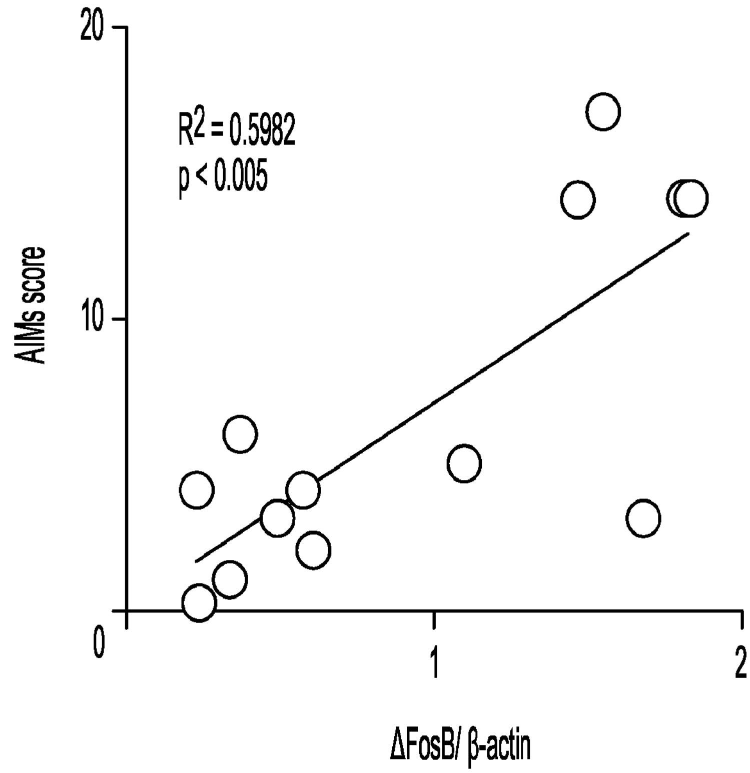
FIG. 8C: Correlation between ΔFosB protein level and AIMs scores. For linear regression analyses, the total AIMs scores taken on the 18th day (highest levels) of the six post-AAV assessments were paired with the relative band intensity expressed in FIG. 8**B for each animal (n=13).

Analysis of striatal tissue confirmed significant repression of ΔFosB in animals injected with AAV-sh[ΔFosB] compared with those injected with the control AAV-sh[NT] vector (FIGS. 8A and 8B). And the level of ΔFosB correlated with the severity of AIMs (FIG. 8C). And the efficiency of virus infection was confirmed by GFP staining in both groups (FIGS. 4D-4E).

Figure 9A:
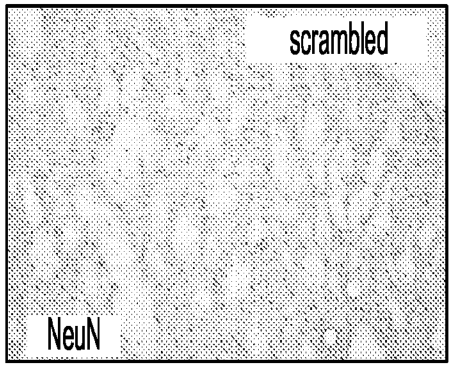
FIGS. 9A, 9B, 9C, 9D, 9E, 9F, 9G and 9H are a series of immunofluorescence images showing virus injection in the striatum induced no tissue damage.
Figure 9B:
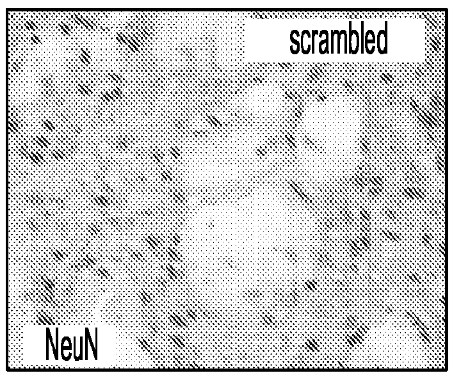
Figure 9C:
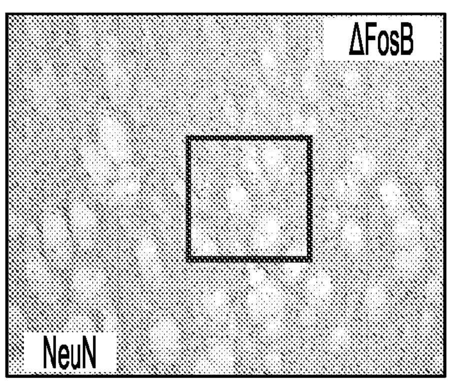
Figure 9D:
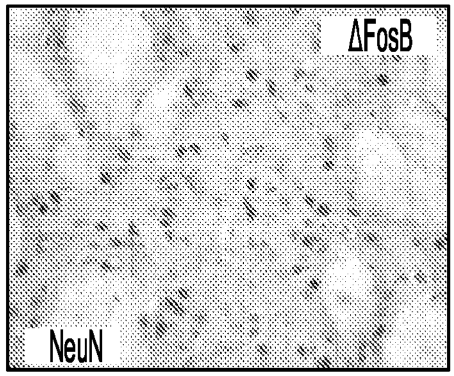
Figure 9E:
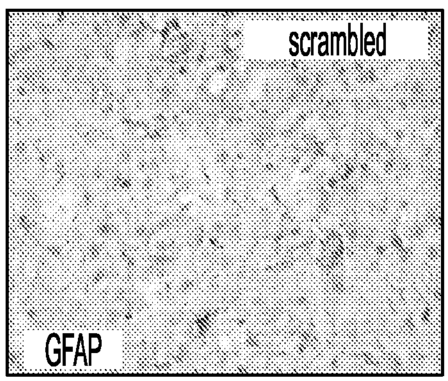
Figure 9F:
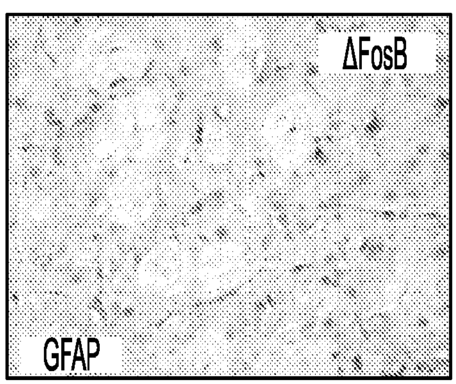
Figure 9G:
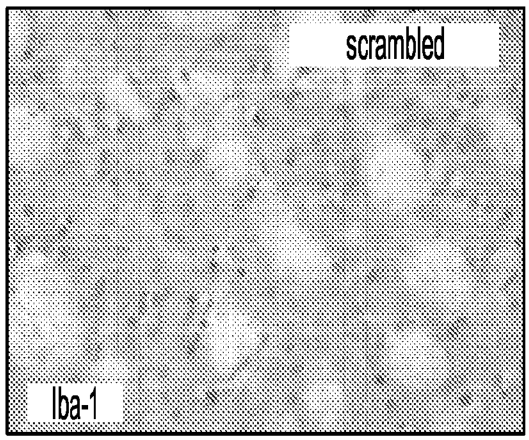
Figure 9H:
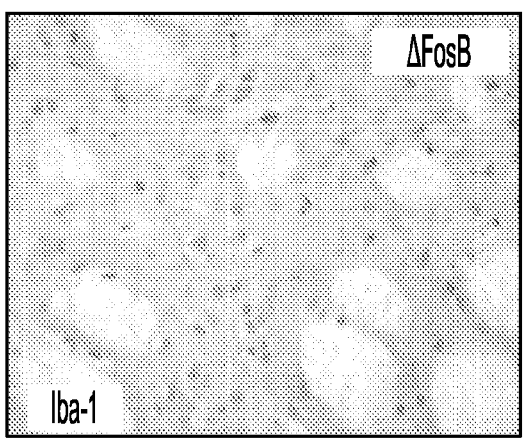

No AAV-shRNA-mediated toxicity was observed in the striatum. Previous studies have showed that some shRNAs caused lethal toxicity in the rodent striatum. In this study, immunohistochemical analyses were performed using primary antibodies against NeuN (neuronal marker), GFAP, and Iba-1. In the striatum of rats in the two groups, striatal neuronal loss (FIGS. 9A-9D), reactive astrogliosis (FIGS. 9E and 9F), or microglial infiltration (FIGS. 9G and 9H) were not observed. These results suggest that the shRNA is not toxic and is suitable for clinical application.

In summary, striatal gene knockdown of ΔFosB using rAAV expressing a specific shRNA reduced the development of AIMs induced by L-Dopa in the rat model of PD in comparison with rats with intra-striatal infusion of control virus. Injections of rAAV-shRNA ΔFosB as well as control virus had no impact on motor deficits induced by 6-OHDA lesion or anti-parkinsonian action of L-Dopa. The viruses used in the present study showed no neuronal toxicity. It was confirmed that there was no neuronal loss, astrogliosis, or microglial activation with both rAAV-shRNA ΔFosB and rAAV-scrambled shRNA. The results also showed that expression levels of striatal ΔFosB had no significant effect on the anti-parkinsonian effect of L-Dopa, suggesting that gene silencing of striatal ΔFosB would participate only in the improvement of LID and not affect pharmacological actions of L-Dopa to improve parkinsonian motor deficits. This is the first report to show the effect of gene silencing specifically of ΔFosB in the striatum on the development of LID. These results suggest that rAAV-mediated gene silencing of ΔFosB is a safe and effective therapeutic approach for LID in PD patients.

Other Embodiments

All nucleic acids, nucleic acid names, genes, gene names, and gene products disclosed herein are intended to correspond to homologs from any species for which the compositions, viruses, vectors, kits, and methods disclosed herein are applicable. Thus, the terms include, but are not limited to, nucleic acids, genes and gene products from humans and rodents. It is understood that when a nucleic acid, gene or gene product from a particular species is disclosed, this disclosure is intended to be exemplary only, and is not to be interpreted as a limitation unless the context in which it appears clearly indicates. Any improvement may be made in part or all of the compositions, viruses, vectors, kits, and method steps. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A recombinant viral vector comprising (a) a heterologous polynucleotide sequence comprising a nucleic acid sequence encoding at least one shRNA specific for ΔFosB, wherein the at least one shRNA has at least 90% or more sequence identity with the sequence of SEQ ID NO: 1 or at least 90% or more sequence identity with the sequence of SEQ ID NO: 2, and (b) inverted terminal repeat (ITR) sequences flanking the heterologous polynucleotide sequence.

2. The recombinant viral vector of claim 1, wherein the at least one shRNA comprises an shRNA comprising the sequence of SEQ ID NO: 4.

3. The recombinant viral vector of claim 1, wherein the recombinant viral vector is a recombinant Adeno-Associated Virus (rAAV) vector or a recombinant lentiviral vector.

4. The recombinant viral vector of claim 1, wherein the at least one shRNA comprises an shRNA having at least 90% or more sequence identity with the sequence of SEQ ID NO: 1 and an shRNA having at least 90% or more sequence identity with the sequence of SEQ ID NO: 2, and wherein the heterologous polynucleotide sequence further comprises a loop sequence.

5. A recombinant lentivirus comprising the recombinant viral vector of claim 1.

6. A rAAV comprising the recombinant viral vector of claim 1.

7. The rAAV of claim 6, wherein the rAAV comprises capsid proteins from a serotype selected from the group consisting of: AAV1, AAV2, AAV3, AAV4, AAV5, AAV6, AAV7, AAV8, AAV9, AAV10, AAV11, AAV12, AAV13.

8. A pharmaceutical composition comprising the rAAV of claim 6.

9. A method of reducing ΔFosB expression in a cell comprising contacting the cell with the rAAV of claim 6.

10. A method of treating dyskinesia in a subject comprising administering to the subject the rAAV of claim 6.

11. The method of claim 8, wherein the dyskinesia is L-Dopa induced dyskinesia.

12. The method of claim 10, wherein the subject is a mammal and the mammal has Parkinson's disease, and administration of the rAAV of claim 6 decreases or eliminates abnormal involuntary movements in the subject.

13. The method of claim 12, wherein the mammal is administered the rAAV of claim 6 via injection or infusion.

14. A kit comprising:

(a) the rAAV of claim 6 in a therapeutically effective amount to reduce ΔFosB expression in a cell or in the treatment of dyskinesia in a subject;

(b) instructions for use; and (c) packaging.

* * * * *